(12) United States Patent
Al-Mulla et al.

(10) Patent No.: US 8,735,443 B2
(45) Date of Patent: May 27, 2014

(54) METHOD OF TREATING DIABETES-RELATED VASCULAR COMPLICATIONS

(75) Inventors: Fahd Al-Mulla, Safat (KW); Milad Bitar, Safat (KW)

(73) Assignee: Kuwait University, Safat (KW)

(*) Notice: Subject to any disclaimer, the term of this patent is extended or adjusted under 35 U.S.C. 154(b) by 336 days.

(21) Appl. No.: 13/210,319

(22) Filed: Aug. 15, 2011

(65) Prior Publication Data
US 2012/0052051 A1    Mar. 1, 2012

Related U.S. Application Data

(63) Continuation-in-part of application No. 12/289,146, filed on Oct. 21, 2008, now abandoned.

(51) Int. Cl.
*A61K 31/385* (2006.01)
(52) U.S. Cl.
USPC .......................................... 514/440
(58) Field of Classification Search
USPC .......................................... 514/440
See application file for complete search history.

(56) References Cited

U.S. PATENT DOCUMENTS

2008/0253997 A1   10/2008   Thomas

FOREIGN PATENT DOCUMENTS

DE    4343647    6/1995

OTHER PUBLICATIONS

Packer et al., Nutrition, 2001;17(10):888-895.*
Allen et al., FASEB, 2003;17:908-910.*
Esposito et al., Circulation,2002;106:2067-2072.*
Chirino Yl et al. Role of oxidative and nitrosative stress in cisplatin-induced nephrotoxicity. Exp Toxicol Pathol, vol. 61, pp. 223-242 (Abstract only) (2009).
Viles-Gonzalez et al., European Heart Journal, vol. 25, pp. 1197-1207 (2004).
Zhang WJ et al "Dietary alpha-lipoic acid supplementation inhibits atherosclerotic lesion development in Apolipoprotein E-deficient and apolipoprotein-E/Low density lipoprotein receptor-deficient mice." Circulation, vol. 117, pp. 421-428 (2008).
Lee BW et al. "Dose-related cytoprotective effect of alpha-lipoic acid on hydrogen peroxide-induced oxidative stress to pancreatic beta cells." Free Radic Res 43(1): pp. 68-77 (Abstract only) (2009).
Vasdev et al, Journal of Hypertension, vol. 18, pp. 567-573 (2000).

(Continued)

*Primary Examiner* — San-Ming Hui
(74) *Attorney, Agent, or Firm* — Richard C Litman

(57) ABSTRACT

The method of treating diabetes-related vascular complications includes the treatment of diabetic patients with α-lipoic acid (LA) in order to mitigate the negative impact of diabetes-related vascular dysfunctions upon vascular homeostasis. The treatment method includes the step of administering to the patient an initial dosage of α-lipoic acid believed to be therapeutically effective. The patient's response is then monitored by measuring α-lipoic acid-responsive biomarkers and by performing assays from blood and tissue taken from the patient.

3 Claims, 16 Drawing Sheets

(56) References Cited

OTHER PUBLICATIONS

Evans JL et al. "Alpha-lipoic acid: a multifunctional antioxidant that improves insulin sensitivity in patients with type 2 diabetes." Diabetes Technol Ther, vol. 2, pp. 401-413 (Abstract only) (2000).
Packer L et al. "Molecular aspects of lipoic acid in the prevention of diabetes complications." Nutrition, vol. 17, pp. 888-895 (Abstract only) (2001).

Yi X et al. "α-Lipoic acid prevents the increase in atherosclerosis induced by diabetes in apolipoprotein E-deficient mice fed high fat/low cholesterol diet." Diabetes, vol. 55, pp. 2238-2244 (2006).
Kamenova P "Improvement of insulin sensitivity in patients with type 2 diabetes mellitus after oral administration of alpha-lipoic acid." Hormones, vol. 5, pp. 251-258 (2006).

* cited by examiner

```
                         SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: forward primer

<400> SEQUENCE: 1
tcgtagcaaa ccaccaag                                               18

<210> SEQ ID NO 2
<211> LENGTH: 16
<212> TYPE: DNA
<213> ORGANISM: Artificial Sequence
<220> FEATURE:
<223> OTHER INFORMATION: reverse primer

<400> SEQUENCE: 2
ctgacggtgt gggtga                                                 16

<210> SEQ ID NO 3
<211> LENGTH: 18
<212> TYPE: DNA
<213> ORGANISM: Artificial Sequence
<220> FEATURE:
<223> OTHER INFORMATION: forward primer

<400> SEQUENCE: 3
ggatgaatct caggccaa                                               18

<210> SEQ ID NO 4
<211> LENGTH: 16
<212> TYPE: DNA
<213> ORGANISM: Artificial Sequence
<220> FEATURE:
```

-continued

```
<223> OTHER INFORMATION: reverse primer

<400> SEQUENCE: 4
ttagccaagg cttcgg                                                    16

<210> SEQ ID NO 5
<211> LENGTH: 24
<212> TYPE: DNA
<213> ORGANISM: Artificial Sequence
<220> FEATURE:
<223> OTHER INFORMATION: forward primer

<400> SEQUENCE: 5
tgaatcttgc tggttgacac ttgc                                           24

<210> SEQ ID NO 6
<211> LENGTH: 21
<212> TYPE: DNA
<213> ORGANISM: Artificial Sequence
<220> FEATURE:
<223> OTHER INFORMATION: reverse primer

<400> SEQUENCE: 6
gagggacagg tgggagggaa g                                              21

<210> SEQ ID NO 7
<211> LENGTH: 18
<212> TYPE: DNA
<213> ORGANISM: Artificial Sequence
<220> FEATURE:
<223> OTHER INFORMATION: forward primer

<400> SEQUENCE: 7
gaagtgtgac gttgacat                                                  18

<210> SEQ ID NO 8
<211> LENGTH: 17
<212> TYPE: DNA
<213> ORGANISM: Artificial Sequence
<220> FEATURE:
<223> OTHER INFORMATION: reverse primer

<400> SEQUENCE: 8
acatctgctg gaaggtg                                                   17
```

METHOD OF TREATING DIABETES-RELATED VASCULAR COMPLICATIONS

CROSS REFERENCE TO RELATED APPLICATIONS

This is a continuation-in-part of our prior application Ser. No. 12/289,146, filed Oct. 21, 2008.

INCORPORATION BY REFERENCE OF MATERIAL SUBMITTED IN COMPUTER READABLE FORM

The applicants hereby incorporate by reference the sequence listing contained in the ASCII text file titled 23588_LISTING_ST25.txt, created Nov. 1, 2011 and having 1.74 KB of data (2.00 KB size on disk).

BACKGROUND OF THE INVENTION

1. Field of the Invention

The present invention relates to the treatment of diabetes-related vascular complications. The treatment method includes the step of administering to the patient a therapeutically effective dosage of alpha-lipoic acid.

2. Description of the Related Art

Epidemiological and experimental evidence both indicate that diabetes is a major risk factor for the development of atherosclerosis and hypertension, and these clinical scenarios lead to aortic aneurysm, heart failure, myocardial infarction and stroke. It has been shown that the diabetic vascular system is associated with endothelial dysfunction and this phenomenon is considered to be a causal factor in the development of atherothrombotic disease, and as one of the earliest abnormalities that can be detected clinically in an individual predisposed to atherosclerosis and hypertension. However, the exact molecular mechanisms responsible for these changes in vascular phenotype in diabetes remain unknown. Further, treatment intended to reverse or delay diabetes-induced decline of vascular function has yet to be implemented.

Dysfunction of the endothelium in a number of vascular diseases, including diabetes, hypertension, and atherosclerosis, is associated with reduced bioavailability of the signaling molecule nitric oxide, which has potent vasodilatory, anti-inflammatory and antiatherosclerotic properties. A large quantity of available evidence indicates that impaired endothelium-derived NO bioavailability is due, in part, to excess oxidative stress. Diseased blood vessels produce increased levels of reactive superoxide anion ($O_2^-$) and hydrogen peroxide. Superoxide anion reacts with NO, yielding peroxynitrate, which has the potential of inducing protein modification, DNA damage, apoptosis and inflammation.

Oxidative stress in a physiological setting reflects an excessive bioavailability of Reactive Oxygen Species (ROS), which is the net result of an imbalance between production and destruction of ROS, with the latter being influenced by antioxidant defenses, including antioxidant enzyme (e.g., superoxide dismutase, glutathione peroxidase, and catalase) and chemical antioxidants (e.g., α-lipoic acid (LA) and vitamins). Excessive stress has been shown to promote apoptosis and elicits several inflammatory responses in endothelial cells, including the production of proinflammatory responses in endothelial cells, including the production of proinflammatory cytokines and chemokines TNF-α, IL-1β, along with monocyte chemoattractive protein (MCAP-1 or MCP-1), and an increased surface expression of the cellular adhesion molecules, E-selectin, vascular cell adhesion molecule 1 (VCAM-1) and intracellular adhesion molecule (CAM or ICAM-1). A large portion of the above parameters are altered as a function of diabetes.

Alpha-lipoic acid (LA) is an endogenous short-chain fatty acid that occurs naturally in the human diet and is rapidly absorbed and converted intracellularly to dihydrolipoic acid via NAD(P)H-dependent enzymes. In addition to playing an important role as a cofactor for mitochondrial bioenergetic enzymes, LA and dihydrolipoic acid can scavenge ROS, regenerate other natural antioxidants, such as glutathione, vitamin C and vitamin E, chelate metals ions, and stimulate insulin signaling. LA further improves neurovascular and metabolic abnormalities and may further play a role in cardiovascular protection and as an anti-inflammatory agent. Additionally, it has been shown that LA ameliorates diabetes-related deficits in skeletal muscle glucose metabolism, protein oxidation, as well as the activation by insulin of the various steps of the insulin signaling pathway, including the enzymes AKT/PKB and phosphatidyl inositol 3-kinase.

Thus, a method of treating diabetes-related vascular complications solving the aforementioned problems is desired.

SUMMARY OF THE INVENTION

It has been found that a heightened state of oxidative stress, either acting alone or in concert with augmented apoptotic and inflammatory processes, contributes to diabetes-related vascular dysfunction. The method of treating diabetes-related vascular complications includes the treatment of diabetic patients with alpha-lipoic acid (LA) (sometimes alternately written as α-lipoic acid) in order to mitigate the negative impact of diabetes-related vascular dysfunctions upon vascular homeostasis. The treatment method includes the step of administering to the patient a therapeutically effective dosage of alpha-lipoic acid.

In human patients, the initial dosage of alpha-lipoic acid is preferably between approximately 100 and 300 mg., delivered daily. Although the alpha-lipoic acid may be injected in solution, it is preferably delivered orally to the patient.

In order to monitor and adjust the treatment, the method provides for determining the efficacy of an alpha-lipoic acid treatment for treating a subject suspected of suffering from diabetes-related vascular complications, which includes determining a level of one or a combination of various inflammatory or apoptotic biomarker(s) in a sample(s) obtained from the subject following administration of alpha-lipoic acid. The sample is compared with the level of the biomarker(s) in a sample(s) obtained from a subject with a known standard level of the inflammatory or apoptotic biomarker associated with diabetes related vascular complications. A lower level of the inflammatory or apoptotic biomarker in the sample(s) from the subject relative to the known standard level of the inflammatory or apoptotic biomarker indicates that the alpha-lipoic acid treatment is efficacious for the treatment of diabetes-related vascular complications in the subject.

The method can be used to treat any mammal suffering from diabetes-related vascular complications, but most preferably the patient is human. Various biomarkers have been determined by the inventors to indicate a response to alpha-lipoic acid in a patient suffering from a diabetes-related vascular complication. The biomarkers include NRF2, TNF-α, IL-1β, IL-6, MCP1, FKN, NF-κB, caspase 3, caspase 7, pg-91$^{phox}$, Nox-1, ICAM-1, PI3K and Akt.

A response to administration of alpha-lipoic acid can also be determined through one or more of the following: a DNA fragmentation assay, a superoxide cytochrome c assay, a NADPH oxidase activity assay, an acetylcholine-induced tissue relaxation assay, a reactive oxygen-induced ethidium bromide fluorescence assay, and any combination thereof. These can be used to analyze patient samples, such as whole blood, plasma, serum, blood product, or cellular or tissue samples.

The sample can be compared to a known standard level taken from the patient suspected of suffering from diabetes-related vascular before beginning alpha-lipoic acid treatment, or the known standard can be derived from other patients suffering from diabetes-related vascular complications.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
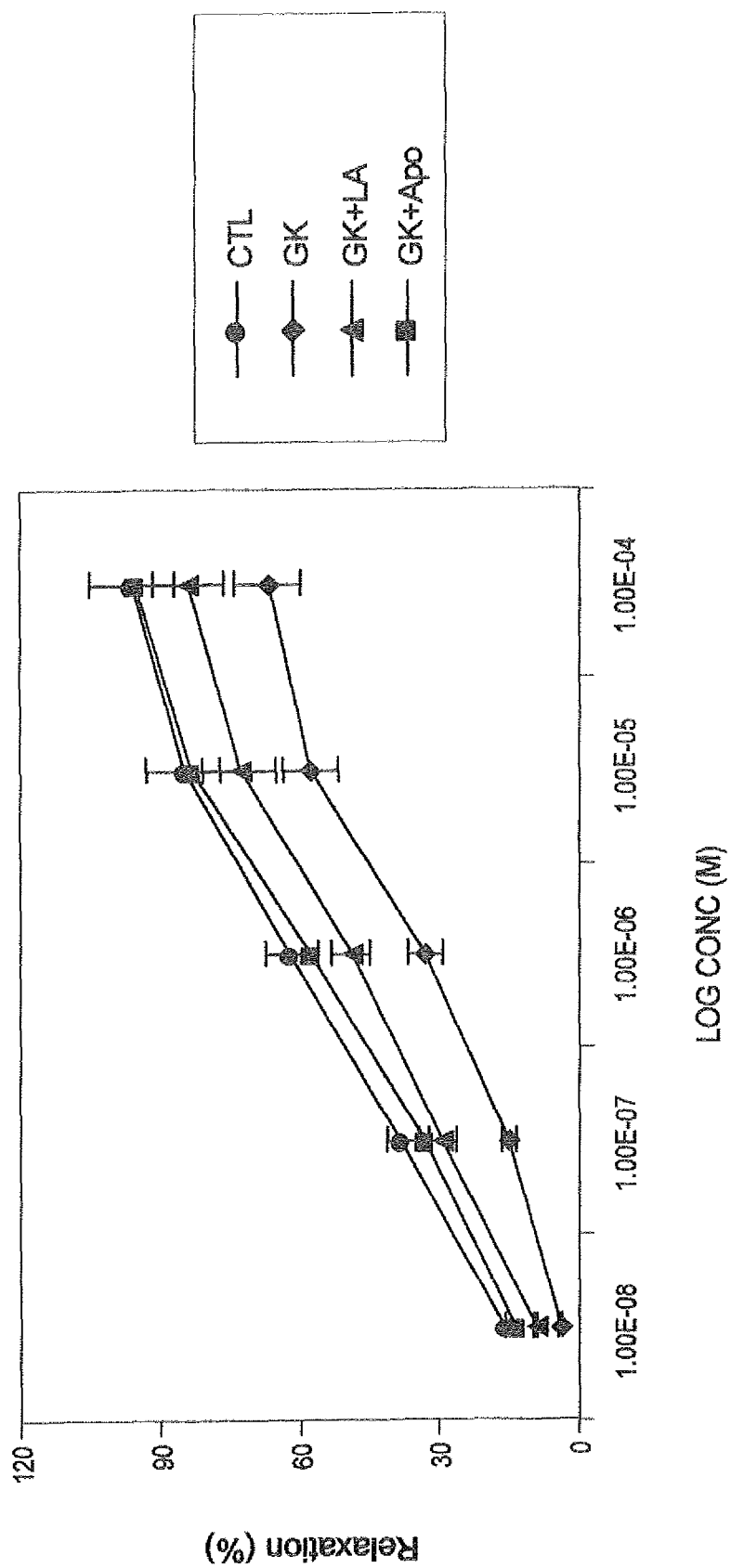
FIG. 1 is a data plot illustrating relaxation in aortic vessels as a function of maximum norepinephrine-induced vasoconstriction.

The present invention is directed towards a method of treating diabetes-related vascular complications. It has been found that a heightened state of oxidative stress, either acting alone or in concert with augmented apoptotic and inflammatory processes, contributes to diabetes-related vascular dysfunction. The present invention is directed towards the treatment of diabetic patients with alpha-lipoic acid in order to mitigate the negative impact of the above dysfunction upon vascular homeostasis. The treatment method includes the step of administering to the patient a therapeutically effective dosage of alpha-lipoic acid. The patient's progress may be monitored by testing various biomarkers disclosed herein or performing various cell assays disclosed herein, and the treatment may be adjusted accordingly.

It has been further found that diabetic aortic tissue exhibits a decline in acetylcholine-induced relaxation and a heightened state of oxidative stress (as exemplified by an increase in NAD(P)H oxidase activity and expression), elevation in the levels of protein-bound carbonyl and thiobarbituric acid reactive substance, along with an enhancement in the rate of superoxide production, aortic DNA fragmentation rate and caspase 3/7 activity. Further, sensitive indicators of the rate of apoptotic cell death are augmented as a function of diabetes. Similarly, an up-regulation in vascular inflammatory markers, including TNF-α, IL-6, intracellular adhesion molecule 1 and monocyte chemoattractant protein-1 (MCAP-1), is evident in this disease state.

Additionally, an assessment of nuclear factor kappa 13 activity (NF-κB) reveals a marked accumulation of this transcriptional factor in aortic nuclear extracts of diabetic rats. At least a portion of the above abnormalities may be reversed following a chronic treatment of the diabetic patient with LA.

In aortic tissue of control animals, it has been found that TNFα elicits endothelial dysfunction, augmented state of oxidative stress, increased apoptosis and pro-inflammatory gene expression, mimicking in many respects the clinical features of diabetic vessels. Thus, it can be concluded that LA exerts vasculoprotective effects, possibly via mechanisms involving the down regulation of the TNFα/NF-κB signaling pathway. It has further been concluded that α-lipoic acid mitigates the negative impact of the aforementioned phenomena upon diabetic vascular homeostasis through the PI3K/Akt signaling pathway.

In the below, a study has been performed to examine the reversing or delaying of certain pathophysiological features of diabetes-mediated endothelial dysfunction in the therapeutic context of chronic intraperitoneal administration of LA to Goto-Kakizaki (GK) rats, a generic animal model of non-obese type II diabetes. Although the below experimental data and descriptions are based upon rat physiologies, extrapolated for human usage, the proper initial dosage in humans is preferably between approximately 100 mg and 300 mg, taken daily. Although alpha-lipoic acid may be injected in solution, the patient preferably receives the dosage orally.

In the experiments, with regard to animals and drug treatment, animal studies were performed in accordance with the National Institutes of Health Guidance for the care and use of laboratory animals. Type II diabetic GK rats were produced by selective inbreeding of glucose-intolerant Wistar rats. All offspring of GK animals are similarly affected by mild hyperglycemia within the first two weeks of birth. Weight-matched male Wistar rats served as a control. Three groups of animals were studied: vehicle-treated Wistar rats (n=8), vehicle-treated GK rats (n=10) and LA-treated GK rats (n=12). LA at a concentration of 50 mg./kg., i.p. (Calbiochem La Jolla Calif.) dissolved in tris-base and adjusted to a pH of 7.4 was injected daily for a duration of four weeks. All rats were maintained under a 12-hour light-dark cycle and had free access to water and a standard rodent's diet.

In the experiments, with regard to the determination of endothelium dependent relaxation (EDR) in the aorta, EDR in response to various concentrations of acetylcholine (Ach) ($10^{-9}$ to $10^{-6}$ mol/l) was assessed in norepinephrine ($10^{-7}$ mol/l) preconstructed rat aortic rings using an organ chamber bath. The effects of the NAD(P)H oxidase inhibitor apocynin ($3\times10^{-4}$ mol/l) and the $O_2^-$ scavenger Tiron (10 mmol/l) on Ach-induced responses of diabetic arteries were also considered.

In the study, with regard to measurement of vascular superoxide anion formation, $O_2^-$ concentration in aortic tissue was determined using a lucigenin-enhanced chemiluminescence method, and the resulting data were further confirmed by a cytochrome c-based technique. Segments of the thoracic aorta were placed into 2 ml Krebs-Henseleit buffer (KHB, pH 7.4), and prewarmed to 37° C. for one hour. Immediately before measurement, rings were transferred to scintillation vials containing KHB with 5 μmol/L lucigenin and the $O_2^-$ generated chemiluminescence was recorded for five minutes with a scintillation counter. The amount of $O_2^-$ produced was quantified using a standard curve of $O_2^-$ generation by xanthine/xanthine oxidase and the data are expressed as nmol per min, per mg, of wet weight. In some experiments, vessels were denuded of endothelium by gentle rubbing of the luminal surface, whereas in others, $N^\omega$-nitro-L-arginine methyl ester (L-NAME) 0.1 mM, diphenylene iodonium 0.1 mM, or apocynin 3 mM were added 60 min before determining $O_2^-$ generation.

Dihydroethidium (DHE), an oxidative fluorescent dye, was used to localize superoxide production in situ. DHE is oxidized on reaction with superoxide to ethidium bromide, which binds to DNA in the nucleus and fluoresces. Arteries were embedded in OCT medium, frozen and cryosectioned. Vascular sections were incubated with DHE at a concentration ($10^{-6}$ mol/l) at 37° C. for 30 minutes. DHE images from serial sections were obtained using a Zeiss Axioplan 2000 fluorescence microscope.

Superoxide production was also determined using the superoxide dismutase (SOD)-inhibitable cytochrome c assay. Three to four aortic ring segments (2 mm.) were placed in a buffer containing (in mM) NaCl 145, KCl 4.86, $Na_2HPO_4$ 5.7, $CaCl_2$ 0.54, $MgSO^4$ 1.22, glucose 5.5, deferoxamine mesylate 0.1, and 1 U/ml catalase. Cytochrome c (50 μM) was added and the reaction mixture was incubated at 37° C. for 60 min. with or without SOD (200 U/ml). Cytochrome c reduction was measured by reading absorbance at 550 nm. $O_2^-$ formation in nmol/mg protein was calculated from the difference between absorbance with or without SOD, and the extinction coefficient for change of ferricytochrome c to ferrocytochrome c, i.e., 21 mM/cm$^{-1}$.

Determination of NAD(P)H oxidase activity in the aorta was determined based on superoxide induced lucigenin photoemission. Enzyme assays were carried out in a final volume of 1 ml. containing (in mM) 50 phosphate buffer; pH 7.0, 1 EGTA, 150 sucrose, 0.5 lucigenin, 0.1 NAD(P)H and tissue homogenate. Enzyme reactions were initiated with the addition of lucigenin. Photoemission, expressed in terms of relative light units (RLU), was measured every 5 min. using a luminometer. All assays were carried out in the dark at room temperature. NADPH oxidase-derived $O_2^-$ was confirmed using the flavo protein inhibitor diphenyleneiodinium, which reduced production of $O_2^-$ by >95% in the homogenate.

NADPH oxidases, the primary catalysts for the generation of reactive oxygen species (ROS), in terms of activities and levels of mRNA expression (e.g., nox-1, gp91$^{phox}$ subunits) together with the established indices of oxidative stress (e.g. protein-bound carbonyls, thiobarbituric acid reactive substance), were elevated in aortic tissue of the GK diabetic rats. An assessment of the dynamic status of nuclear factor kappa B (NF-κB) in aortic tissues revealed that the diabetic state promotes its nuclear localization with a concomitant increase in NF-κB-DNA binding activity. A substantial decrease in vascular activity of PI3K and its down stream target p-Akt was evident as a function of diabetes. Most of the aforementioned vascular abnormalities in diabetic animals were ameliorated following chronic LA therapy. It should be noted that wortmannin, a known inhibitor of PI3K, given chronically to GK rats, negated the anti-inflammatory and anti-apoptotic actions of LA. In aortic tissue of control animals, TNFα elicited endothelial dysfunction, augmented state of oxidative stress, increased apoptosis and pro-inflammatory gene expression, mimicking in many respects the clinical features of diabetic vessels. Thus, it can be concluded that LA exerts vasculoprotective effect in diabetic animals by activating the PI3K/Akt signaling pathway.

Further, with regard to quantitative real-time polymerase chain reactions (PCR) in the study, total RNA from the arterial samples was isolated using TRIZOL® reagent, and RNA integrity was verified by agarose gel electrophoresis and quantified by spectrophotometry. Reverse transcription reaction of total RNA (5 μg) was performed using a superscript 111 first-strand synthesis system. Quantitative real-time PCR was performed using fast SYBR Green QPCR. Specific primers were as follows: TNF-α sense, 5'-TCG TAG CAA ACC ACC AAG-3' (SEQ ID NO:1) and antisense, CTG ACG GTG TGG GTG A-3' 5'-CTG ACG GTG TGG GTG A-3' (SEQ ID NO:2); gp 91$^{phox}$ sense, 5'-GGA TGA ATC TCA GGC CAA-3' (SEQ ID NO:3) and antisense 5'-TTA GCC AAG GCT TCG G-3' (SEQ ID NO:4); nox 1 sense, 5'TGA ATC TTG CTG GTT GAC ACT TGC-3' (SEQ ID NO:5) and antisense, 5'-GAG GGA CAG GTG GGA GGG AAG-3' (SEQ ID NO:6); beta-Actin sense, 5'-GAA GTG TGA CGT TGA CAT-3' (SEQ ID NO:7) and antisense, 5'-ACA TCT GCT GGA AGG TG-3' (SEQ ID NO:8).

The housekeeping gene beta-actin was used for internal normalization. Fidelity of the PCR reaction was determined by melting temperature analysis. PCR efficiency for each primer pair was determined by quantitating amplification with increasing concentration of template cDNA. A non-template control served as negative control to exclude the formation of primer dimers or any other non-specific PCR products. RNA expression of target genes was calculated based on the real-time PCR efficiency E and the threshold crossing point (CP) and is expressed relative to the reference gene beta-actin.

With regard to lipid peroxidation, aortic tissues were homogenized in ice-cold tris-hydrochloric acid/buffer (pH 7.4) and butylated hydroxytoluene (BHT). Homogenates were centrifuged at 3,000×g at 4° C. for 10 min. An aliquot of the supernatant was combined with N-methyl-2-phenylindol (10.3) mmol/l in acetonitrile and methanol in the presence of methane sulfonic acid and BHT and the amount of malondialdehyde and 4-hydroxy-2-nonenal was assessed.

With regard to the assessment of apoptotic cell death using enzyme-linked immuno-absorbent-based assay, aortic tissues derived from control, GK and LA-treated GK rats were lysed and cytoplasmic histone-associated DNA fragments, indicating apoptotic cell death were determined by the Cell Death ELISA® plus kit. Data are reported as arbitrary optical density units normalized to protein concentration.

For detection of caspase 3-like activity, protein was isolated and caspase activity was detected in resulting supernatant using an APO-ONE homogenous caspase 3/7 assay (Promega). With regard to subcellular fractionation and western blotting, aortic tissue nuclear extracts were prepared and protein (40 μg) was loaded in each well of 12.1 Tris HO polyacrylamide gel. Separated polypeptide was transferred to nitrocellulose membrane IBio-Rad) and probed with anti NFκB at a 1:2,000 liter. Chemiluminescent detection was performed by an ECL Western Blotting Detection Kit®.

Plasma TNF-α levels from various experimental groups were determined using a rat TNF-α ELISA kit, and tissue protein content was determined using bovine serum albumin as a standard.

To determine the effect of α-lipoic acid on isolated cells from normal and diabetic rats, primary rat fibroblasts were derived from dorsal skin biopsies performed on four diabetic Coto Kakizaki rats (DFs) and four age-matched (12-14 months) and sex-matched (female) Wistar control rats (CFs). After sterilization in povidine solution, the rat skin was washed in sterile water and rinsed in 70% ethanol in phosphate-buffered saline (PBS). The epidermis and dermis were separated following overnight incubation in 0.25% Trypsin/EDTA at 4° C. Samples were washed, diced and digested for thirty minutes at 37° C. in collagenase type I (250 U/ml) dissolved in Dulbecco's modified Eagle medium (DMEM; Invitrogen) containing penicillin (100 U/ml), 2 mM L-glutamine and 26 mM HEPES. After collagenase treatment, the cells were dislodged, centrifuged and resuspended in medium supplemented with 10% fetal bovine serum. The cells were grown under standard conditions, and the medium was changed every three to four days. Control and diabetic fibroblasts were grown under normo-glycemic conditions (5.5 mM glucose) and used in experiments at passage 3 to 5.

Fibroblasts were seeded at $1 \times 10^4$ cells/well on a 96-well plate. After a 24 hour incubation period, the cells were exposed to various concentrations of HP in serum-free medium at 37° C. for 2 hours [lactate dehydrogenase (LDH), a marker for necrotic cell death], or for 16 hours (cell viability). Quantification of cell viability was assessed using a Cell Counting Kit-8 (Dojindo, Kumamoto, Japan). The values obtained were normalized to the vehicle-treated cells. To measure the rate of necrotic cell death, an LDH release assay was performed using a CytoTox-ONE Homogeneous Membrane Integrity Assay kit (Promega). Expression of Nrf2 was inhibited by small-interfering RNA (siRNA) oligonucleotides. The sequences were designed and synthesized by Qiagen. The best silencing efficiency was obtained by incubating 2.0×10 5 cells/well in a 6-well plate with complexes formed by 5 nM siRNA (1 μl) and 9 μL of HiPerfect transfection reagent (Qiagen) dissolved in 90 μl medium, according to the manufacturer's instructions. The transfection was achieved by adding 0.9 ml of medium to the seeded cells followed by 100 μl of siRNA/HiPerfect complex. Knock-out efficiency was verified by real-time PCR and Western blot. Twenty-four hours later, 1 ml of fresh medium was added; 48 hr after transfection the cells were exposed to either vehicle or lipoic acid at a concentration of 500 μM.

With regard to cytokine transcription levels, Total RNA was isolated from cultured fibroblasts using Trizol reagent (Invitrogen) and 1 μg from each sample was reverse transcribed for 1 hr at 37° C. using the High Capacity cDNA Reverse Transcription Kit. Real-time quantitative RT-PCR was performed with the TaqMan Gene Expression Assay and was normalized against 18S RNA using an ABI 7900 Real-time PCR System (Applied Biosystems). Primers and probes were designed by and purchased from Applied Biosystems. Primer efficiency and specificity were verified by amplifying standard dilutions of a probe obtained by pooling all the samples and by melting curve analysis, respectively.

With regard to ELISA assays to determine cytokine expression levels, control and diabetic fibroblasts were seeded on a 6-well plate at $2.5 \times 10^5$ cells/well. After incubation overnight, the cells were treated with or without 50 μM HP in serum/phenol free medium. After incubation for 16 hr, supernatants were collected and analyzed for key inflammatory cytokines, including TNF-α, IL-1β, fractalkine and monocyte chemoattractant protein-1 (MCP-1) using commercially available ELISA kits specific for rats and according to the protocols provided by the manufacturers (R&D and Ray Biotech).

With regard to siRNA studies of Nrf2, expression of Nrf2 was inhibited by small-interfering RNA (siRNA) oligonucleotides. The sequences were designed and synthesized by Qiagen. The best silencing efficiency was obtained by incubating $2.0 \times 10^5$ cells/well in a 6-well plate with complexes formed by 5 nM siRNA (1 μl) and 9 μl of HiPerfect transfection reagent (Qiagen) dissolved in 90 μl medium, according to the manufacturer's instructions. The transfection was achieved by adding 0.9 ml of medium to the seeded cells followed by 100 μl of siRNA/HiPerfect complex. Knock-out efficiency was verified by real-time PCR and Western blot. Twenty-four hours later, 1 ml of fresh medium was added; 48 hr after transfection the cells were exposed to either vehicle or α-lipoic acid at a concentration of 500 μM. At this concentration lipoic acid appears to exert its antinecrotic and anti-inflammatory effects.

Data were normalized with respect to control mean values and expressed as means±SEM. Statistical analyses of data were conducted using the student t-test or by two-way analysis of variance followed by the Tukey post hoc test, as appropriate. Statistical significance was assumed at $P<0.05$.

The experiments conducted in association with the present method have shown that α-LA prevents oxidative stress-induced impairment in endothelial vasodilatory function during diabetes. A decline in acetylcholine (Ach)-induced relaxation of rat aorta was confirmed in GK diabetic rats, a phenomenon appearing to be ameliorated with LA (shown in FIG. 1). This beneficial effect of LA was not evident two weeks after its discontinuation. Both apocyanin and tiron improved Ach-induced relaxation in diabetic arteries, consistent with the concept that up-regulation of NAD(P)H oxidase activity as being responsible, at least in part, for diabetes-induced endothelial dysfunction.

FIG. 1 illustrates relaxation to Acetylcholine(Ach) in aortic vessels of control (CTL), diabetic (GK), and LA-treated diabetic rats (GK+LA). Aortic segments of CTL, GK and GK+LA rats were isolated and their functional performance was assessed within an organ chamber. The graph of FIG. 1 shows force of contraction expressed as percentage of maximum norepinephrine-induced vasoconstriction. Data are expressed as means±SEM of at least 7 animals/group.

Figure 2:
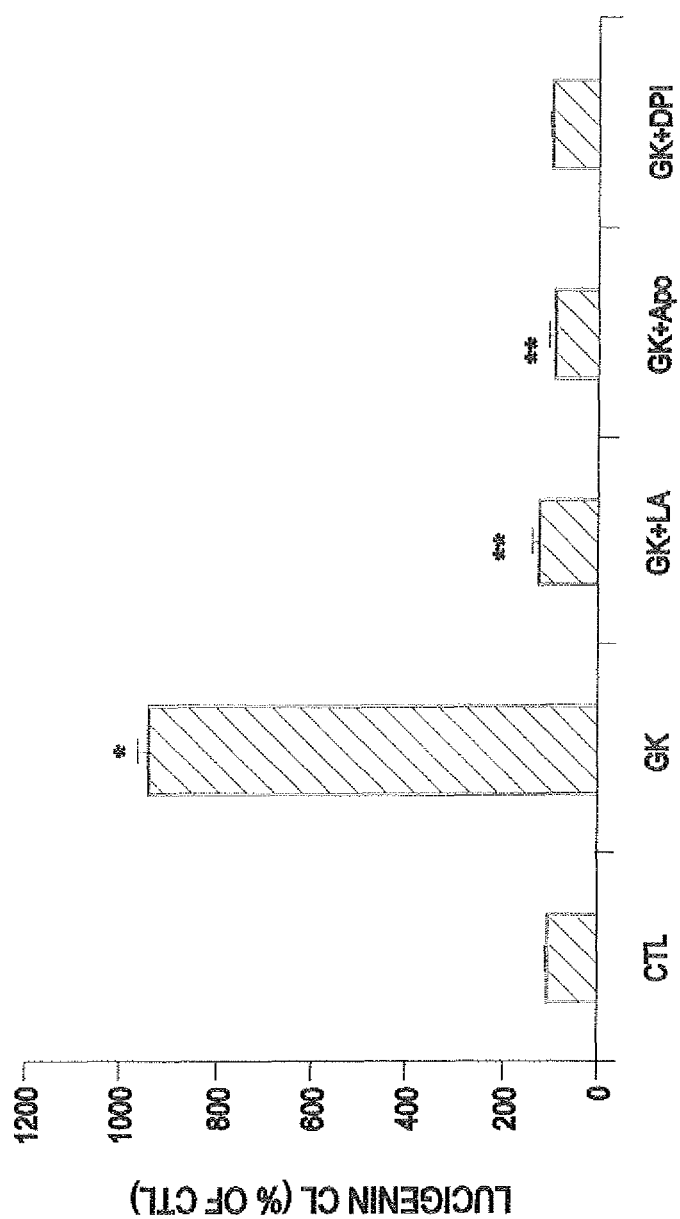
FIG. 2 is a graph illustrating aortic superoxide production in a control sample, a diabetic sample, and in alpha-lipoic acid-treated rats.

Lucigenin chemiluminescence measurement revealed that the aorta of GK diabetic rats exhibited a marked increase in $O_2^-$ production, which was inhibited by apocynin and diphenyleneiodionium, as shown in FIG. 2. FIG. 2 illustrates LA suppression of diabetes-mediated increases in aortic superoxide production in control (CTL), diabetic (GK), and LA-treated diabetic rats (GK+LA). Superoxide production was measured using a lucigenin chemiluminescence-based technique. Data are expressed as means±SEM of at least 7 animals/group. The "*" in FIG. 2 denotes significantly different values from corresponding CTL values at $P<0.05$. The "**" in FIG. 2 denotes significantly different values from corresponding vehicle treated diabetic values at $P<0.05$.

Figure 3:
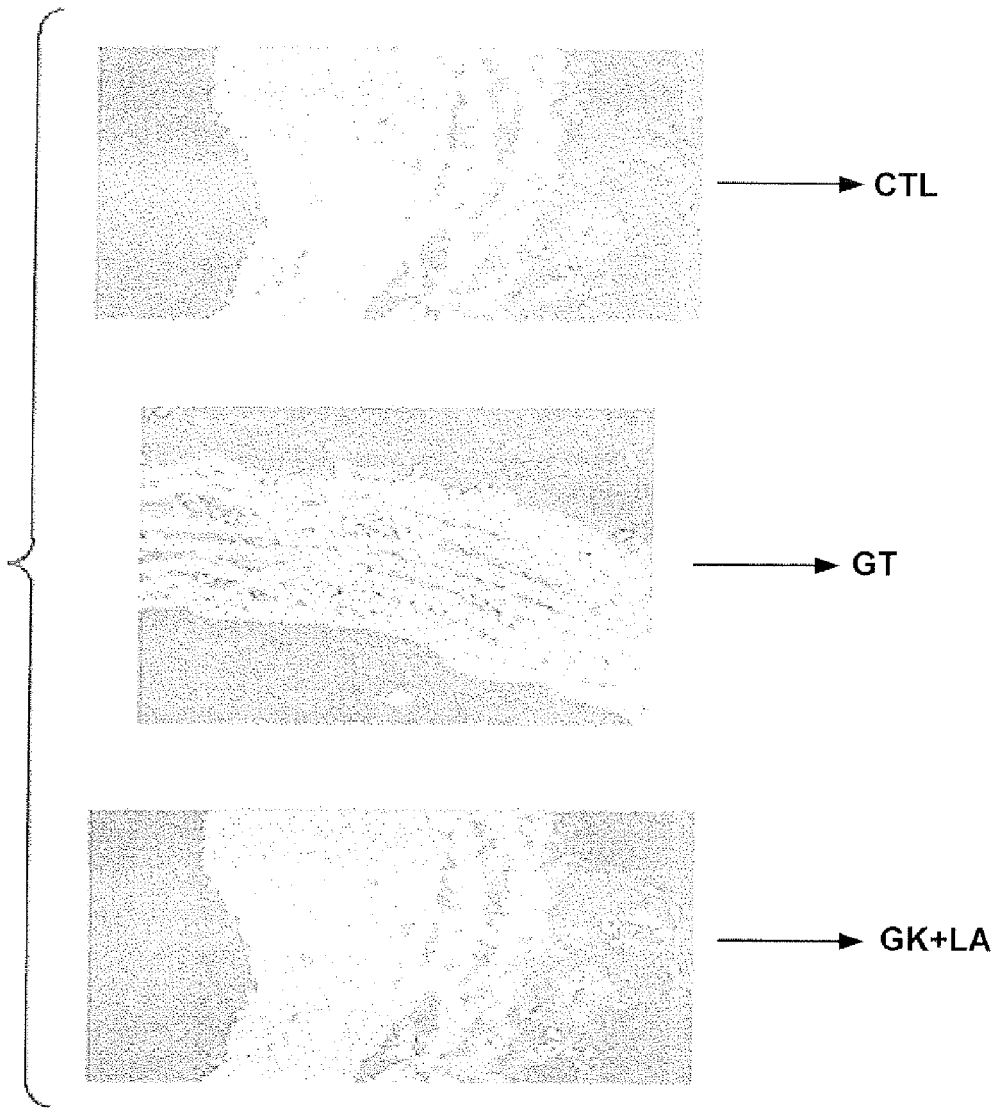
FIG. 3 illustrates ethidium bromide fluorescent photomicrographs of control, diabetic and alpha-lipoic acid-treated diabetic rats.

It should be noted that LA action on diabetic aortic $O_2^-$ generation mimics those produced by apocynin and diphenyleneiodonium. Immunohistochemistry-based techniques revealed that diabetic vessels exhibited a marked increase in the number of ethidium bromide (EB) positive nuclei, both in the endothelium (arrows) and media (smooth muscle cells) when compared to non-diabetic controls, as shown in FIG. 3. Further, nuclear EB fluorescence was significantly reduced in LA-treated diabetic rats. FIG. 3 illustrates ethidium bromide (EB) fluorescent photomicrographs of control (CTL), diabetic (GK), and LA-treated diabetic rats (GK+LA). The photomicrographs show representative images of EB stained nuclei in aortic vessels of CTL, GK and GK+LA rats.

Figure 4:
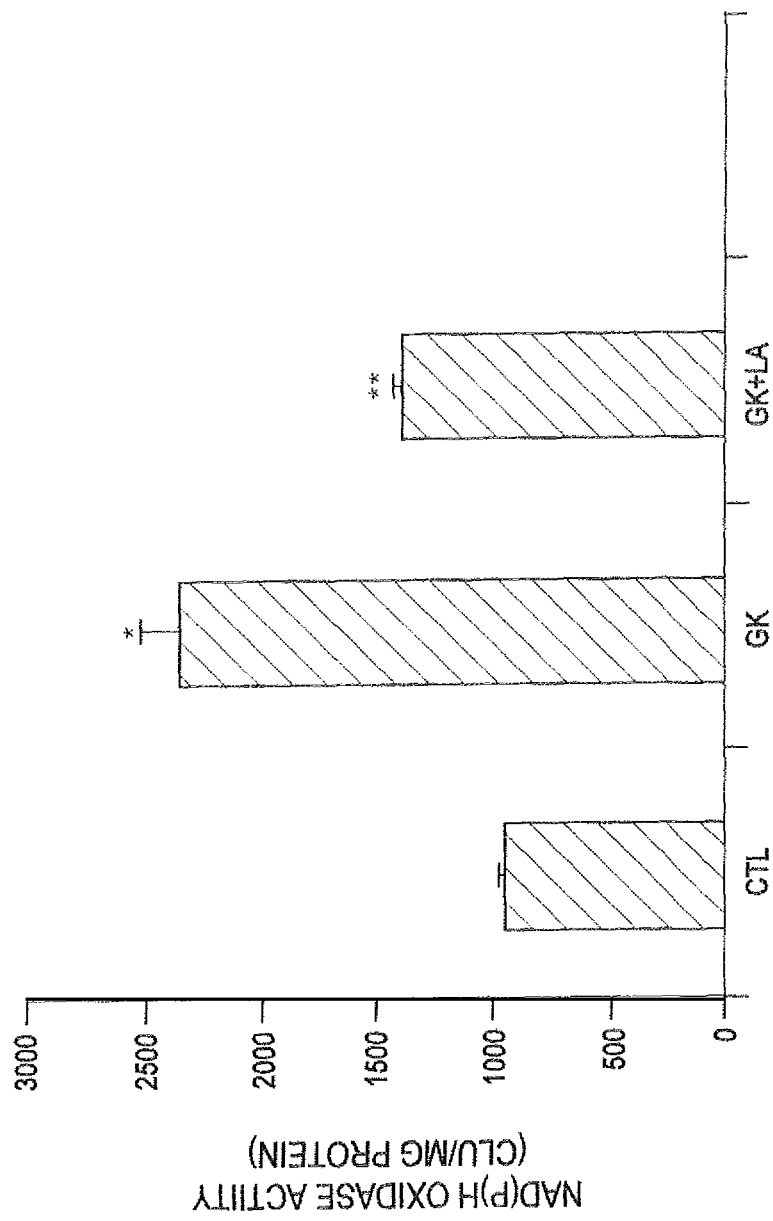
FIG. 4 is a graph illustrating NAD(P)H-based $O_2$ production in aortic homogenates in a control sample, a diabetic sample, and in alpha-lipoic acid-treated rats.
Figure 5A:
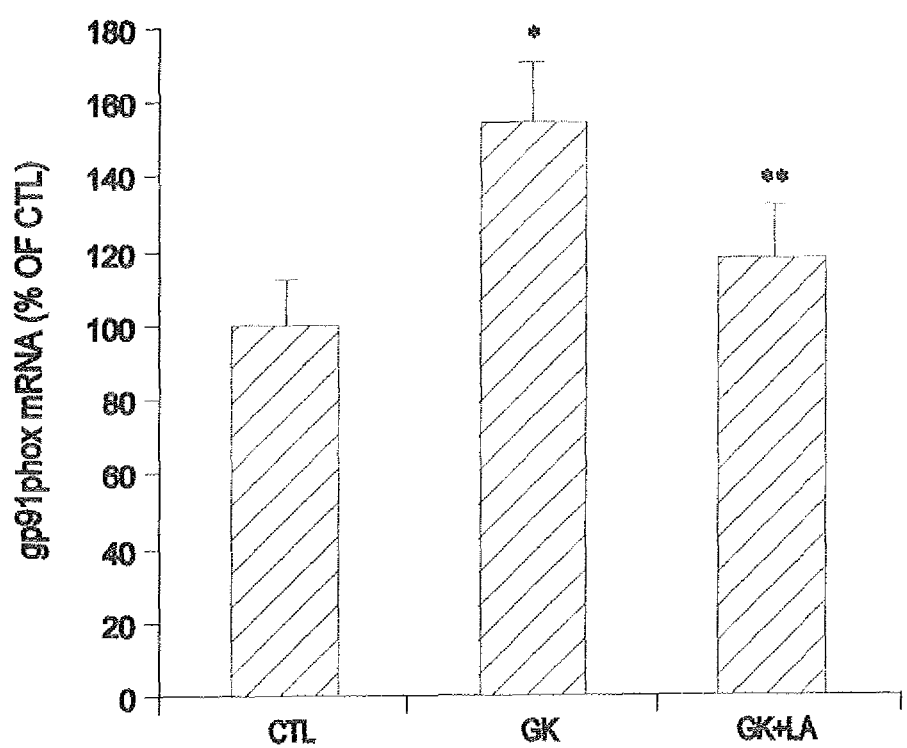
FIG. 5A is a graph illustrating gp $91^{phox}$ concentration in blood vessels in a control sample, a diabetic sample, and in alpha-lipoic acid-treated rats.
Figure 5B:
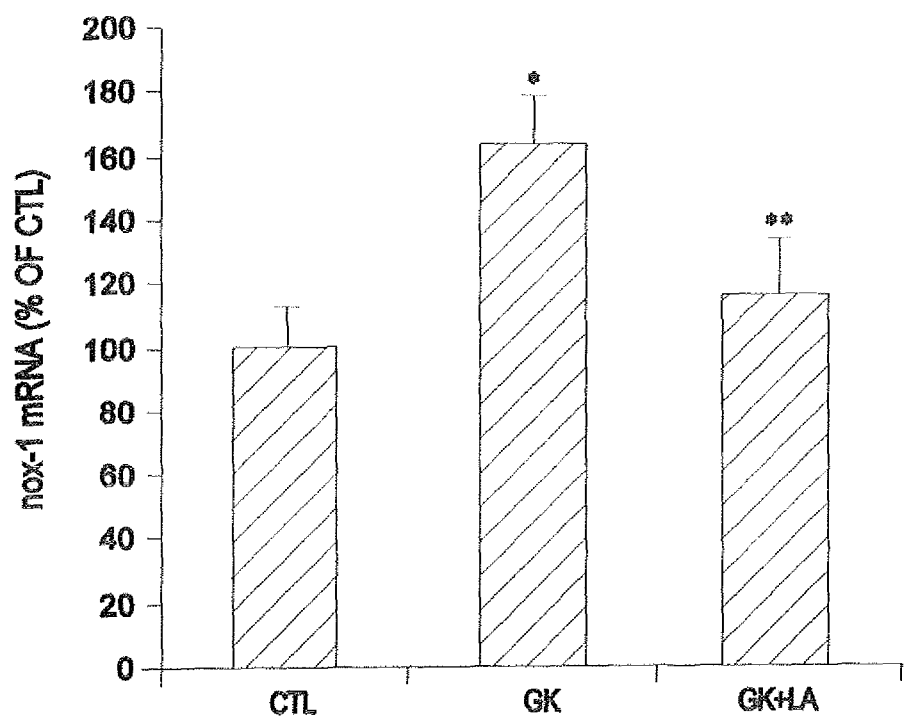
FIG. 5B is a graph illustrating nox-1 concentration in blood vessels in a control sample, a diabetic sample, and in alpha-lipoic acid-treated rats.

Further experimentation assessed NAD(P)H oxidase in terms of activity and gene expression in control, diabetic and α-LA treated diabetic rats. The data revealed an enhancement in NAD(P)H oxidase driven $O_2^-$ generation in homogenates of diabetic aorta, which was significantly attenuated following the institution of LA therapy, as shown in FIG. 4. LA treatment also tended to reduce the rate of gene expression of pg $91^{phox}$, and nox-1 subunits, illustrated in FIGS. 5A and 5B. In FIG. 4, NAD(P)H-based $O_2$ production in aortic homogenates is shown of control (CTL), diabetic, and (GK) LA-treated diabetic rats (GK+LA). Lucigenin chemiluminescence-based techniques were used to measure the rate of aortic $O_2$ generation. Data are expressed as means±SEM of at least 7 animals/group. In FIG. 5A, expression of gp $91^{phox}$ is shown, and in FIG. 5B, expression of nox-1 is shown, both in vessels of control (CTL), diabetic (GK) and LA-treated diabetic rats (GK+LA). Analysis of mRNA expression was performed using RT-PCR based techniques.

Figure 6A:
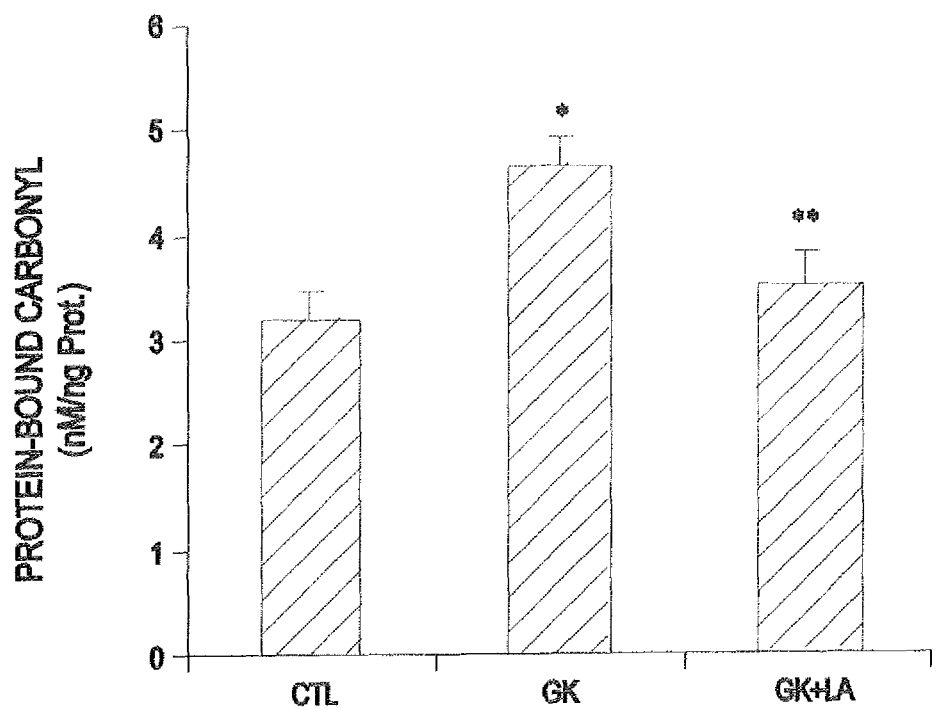
FIG. 6A is a graph illustrating aortic contents of protein-bound carbonyls in a control sample, a diabetic sample, and in alpha-lipoic acid-treated rats.
Figure 6B:
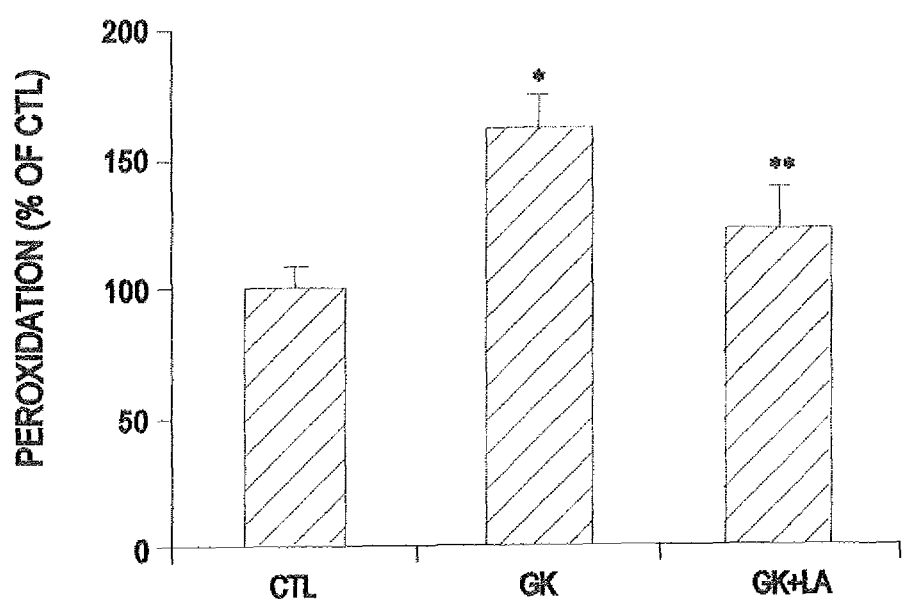
FIG. 6B is a graph illustrating aortic contents of TBARS in a control sample, a diabetic sample, and in alpha-lipoic acid-treated rats.

Overall, the above data are consistent with the concept that the diabetic aorta exhibits a heightened state of oxidative stress. The consequences of this phenomenon upon biological molecules including lipids and proteins were then determined. As can be seen in FIGS. 6A and 6B, the levels of both protein-bound carbonyls and the thiobarbituric acid reactive substances (an indicator of lipid peroxidation) were elevated in diabetic aorta by 45% and 60%, respectively. LA treatment partially reversed the oxidative stress-mediated damage to the lipid and protein molecules during diabetes. FIG. 6A illustrates aortic contents of protein-bound carbonyls in control (CTL), diabetic (GK) and LA-treated diabetic rats (GK+LA), and FIG. 6B illustrates aortic contents of TBARS in control (CTL), diabetic (GK) and LA-treated diabetic rats (GK+LA). Markers of the oxidative stress including protein-bound carbonyls and thiobarbituric acid reactive substances (TBARS) were measured in aortic homogenates. Data are expressed as means±SEM of at least 7 animals/group.

Figure 7A:
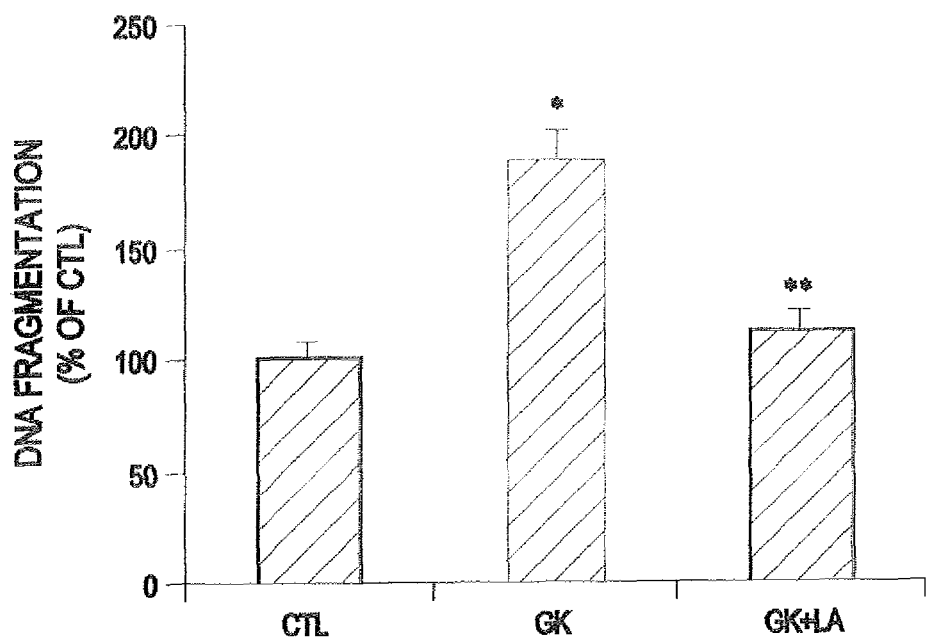
FIG. 7A is a graph illustrating DNA fragmentation in a control sample, a diabetic sample, and in alpha-lipoic acid-treated rats.

The experiments also showed that LA negates diabetes-induced apoptotic cell death. Cytotoxic DNA fragmentation and caspase activities are sensitive indicators of endothelial cell death in blood vessels. Thus, the levels of these parameters were measured in the aorta of various experimental groups including control (CTL), diabetic (GK) and LA-treated diabetic rats (GK+LA). As shown in FIG. 7A, the data reveals that the rate of DNA fragmentation in diabetic specimens was elevated by 75% over corresponding control values. In FIG. 7A, it is shown that LA negates diabetes-dependent increases in DNA fragmentation at caspase 3/7 activity in aortic rat vessels. Markers of apoptotic cell death, including cytoplasmic histone-associated cell death and caspase 3/7 activity (shown in FIG. 7B) were assessed in aortic homogenates. Data are expressed as means±SEM of at least 7 animals/group. Chronic LA treatment significantly reduces DNA fragmentation rate by 42% and caspase 3/7 by 48% in diabetic arteries. This LA-mediated antiapoptotic effect was further markedly reduced two weeks after discontinuation of therapy.

Figure 8A:
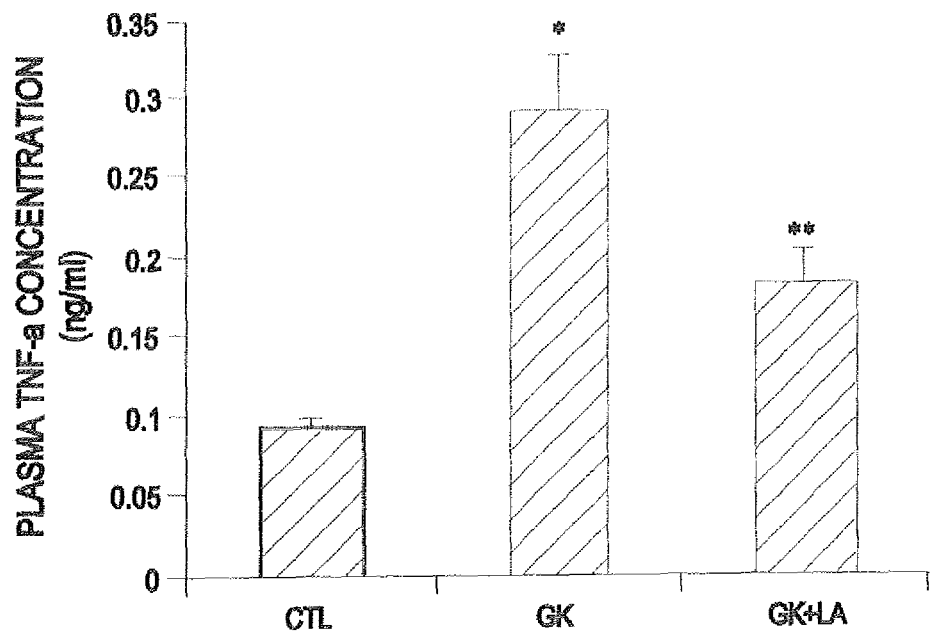
FIG. 8A is a graph illustrating plasma levels in a control sample, a diabetic sample, and in alpha-lipoic acid-treated rats.
Figure 8B:
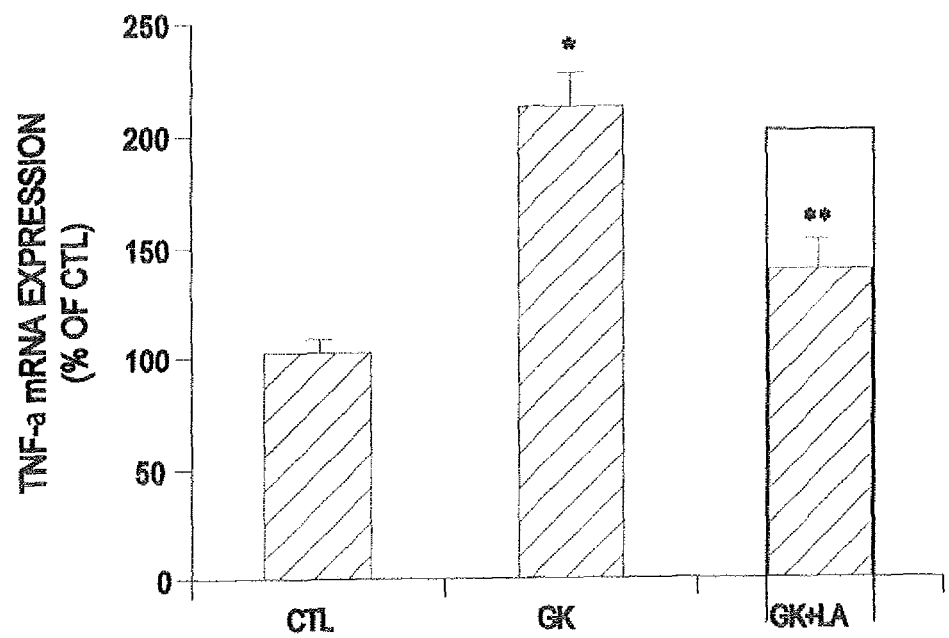
FIG. 8B is a graph illustrating aortic mRNA expression of TNF-α in a control sample, a diabetic sample, and in alpha-lipoic acid-treated rats.

An elevation in NAD(P)H oxidase activity in connection with a high rate of apoptotic cell death during diabetes may stem from vascular proinflammatory phenotype exemplified by enhanced activity of TNF-α. Testing this possibility dictates the assessment of the status of TNF-α in diabetes. The results from these studies confirms that diabetes related up-regulation in the rate of expression of TNF-α, both in terms of protein (plasma) and mRNA (aorta) levels, respectively illustrated in FIGS. 8A and 8B. Reversal of the above abnormalities was achieved by the institution of LA chronic therapy. In FIGS. 8A and 8B, levels of TNF-α were determined in plasma and aorta using, respectively, ELISA and QRT-PCR based techniques. Data are expressed as means±SEM of at least 7 animals/group.

Figure 9A:
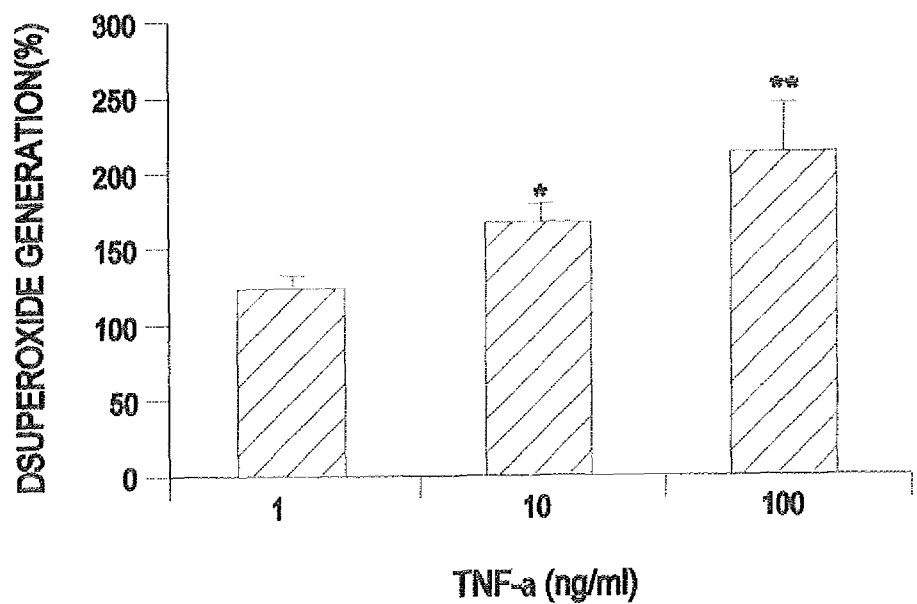
FIG. 9A is a graph illustrating superoxide generation as a function of TNF-α.
Figure 9B:
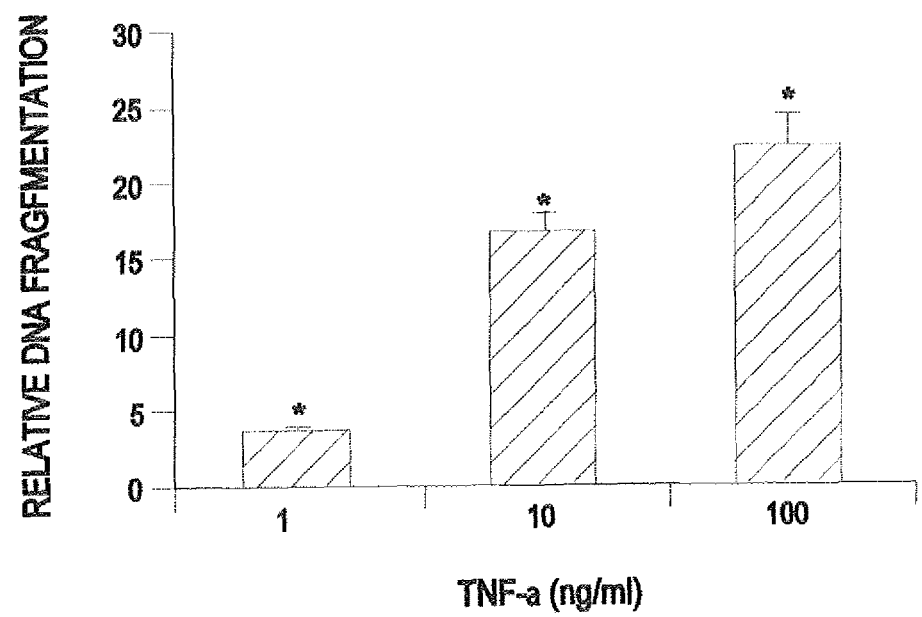
FIG. 9B is a graph illustrating relative DNA fragmentation as a function of TNF-α.
Figure 9C:
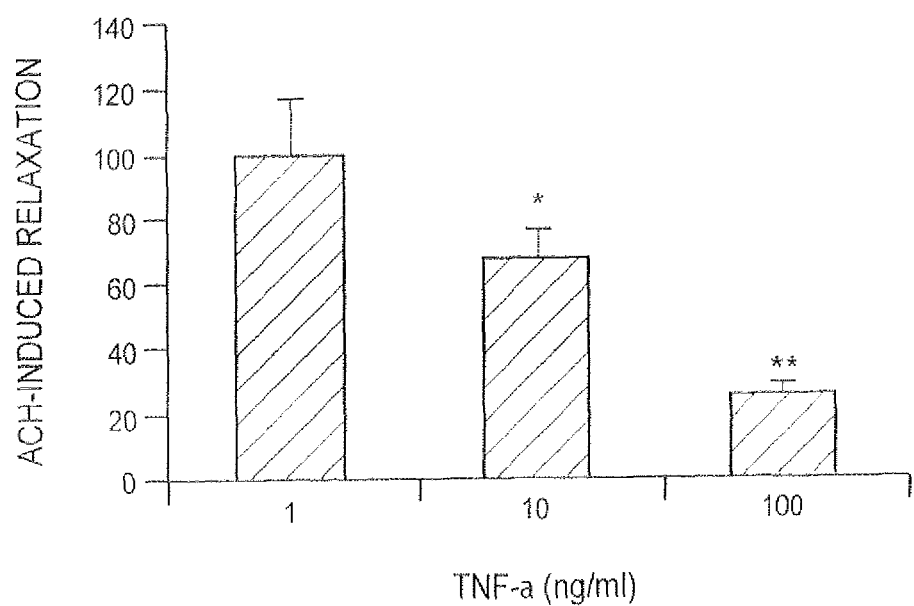
FIG. 9C is a graph illustrating acetylcholine-induced vasorelaxation as a function of TNF-α.

Further, the experiments have found that exogenous TNF-α administration mimics vascular diabetic phenotype. Cultured arteries derived from non-diabetic control animals were exposed in vivo to TNF-α and various other parameters, including: $O_2^-$ generation, Ach-induced relaxation, DNA fragmentation and caspase activity, which were all measured. As shown in FIGS. 9A and 9B, the data reveal that the rate of $O_2^-$ generation, caspase 3/7 activity and the levels of DNA fragmentation were elevated in response to TNF-α treatment. In contrast, this proinflammatory cytokine impaired Ach-induced vasorelaxation (shown in FIG. 9C). It should be noted that pretreatment with LA partially reversed the above TNF-α-induced abnormalities. FIGS. 9A, 9B and 9C illustrate concentration dependence of TNF-α vascular actions. Superoxide generation is shown in FIG. 9A, relative DNA fragmentation is shown in FIG. 9B, and acetylcholine induced vasorelaxation is shown in FIG. 9C. Data are expressed as means±SEM of at least 7 animals/group.

Figure 10A:
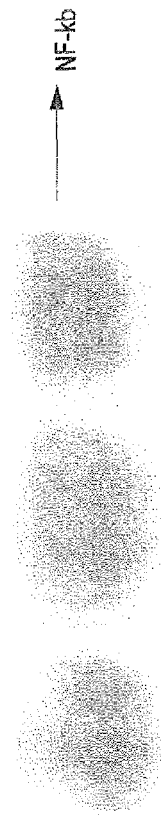
FIG. 10A illustrates western blot analyses of Nf-κB protein expression in aortic tissues of CTL GK and GK+LA rats.
Figure 10B:
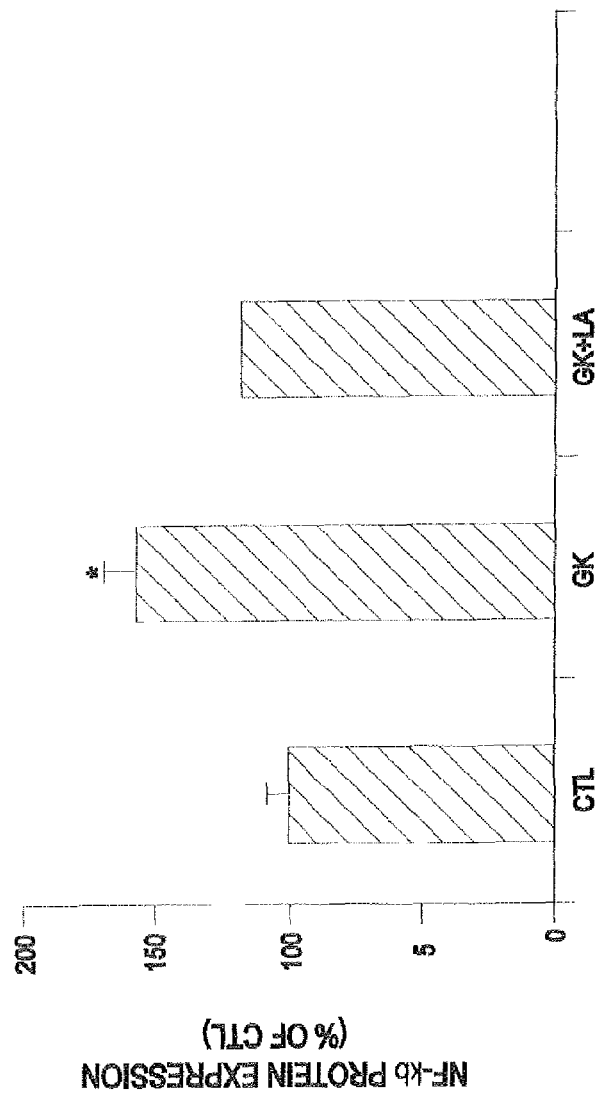
FIG. 10B illustrates averaged densitometric data for a diabetic sample and a sample treated with alpha-lipoic acid expressed as a percentage of change over CTL values.

Further, the experiments revealed that LA mitigates diabetes-induced increases in vascular NF-κB activity. It is well known that TNF-α enhances the activity of NF-κB, most probably via $H_2O_2$ mediated mechanisms. Using data showing that both TNF-α and $H_2O_2$ levels were elevated in diabetic vascular tissues, NF-κB activity was assessed using a western blotting-based technique with an antibody (anti P65) that specifically recognizes the active form of this transcription factor. The data reveals that NF-κB level is high in vascular diabetic nuclei and this abnormality was reversed with LA chronic therapy, as shown in FIGS. 10A and 10B. FIGS. 10A and 10B illustrate aortic nuclear contents of immunoreactive NF-κB in control (CTL), diabetic (GK) and LA treated diabetic rats (GK+LA). Nuclear localization of NF-κB in aortic tissues was determined using differential centrifugation and western blotting-based techniques. FIG. 10A shows representative western blot analyses of Nf-κB protein expression in aortic tissues of CTL, GK and GK+LA rats. FIG. 10B shows averaged densitometric data for GK and GK+LA groups expressed as a percentage of change over the CTL values expressed as 100%. Data are expressed as means±SEM of at least 7 animals/group.

Figure 11A:
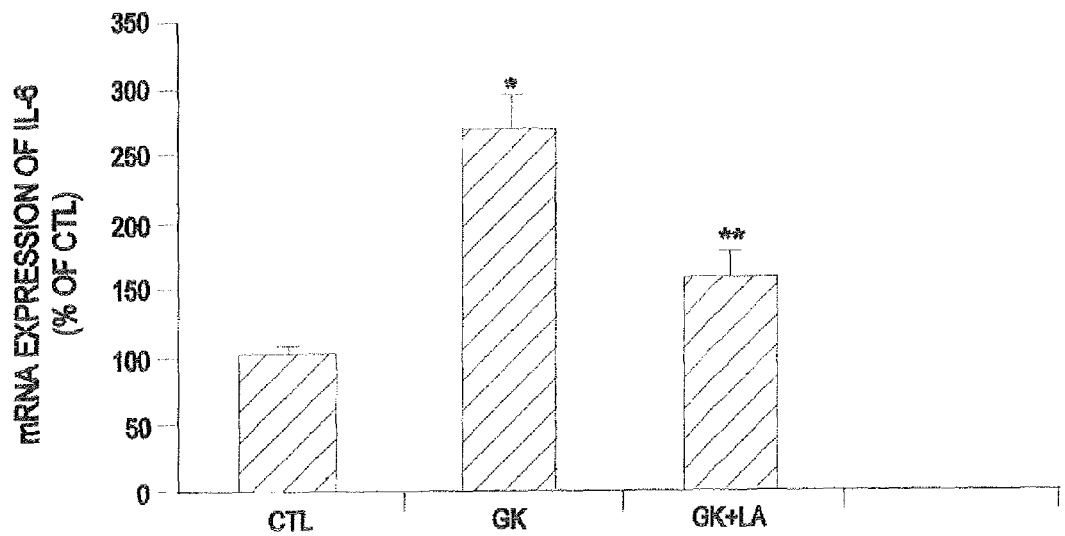
FIG. 11A is a graph illustrating mRNA expression of IL-6 in a control sample, a diabetic sample, and in alpha-lipoic acid-treated rats.
Figure 11B:
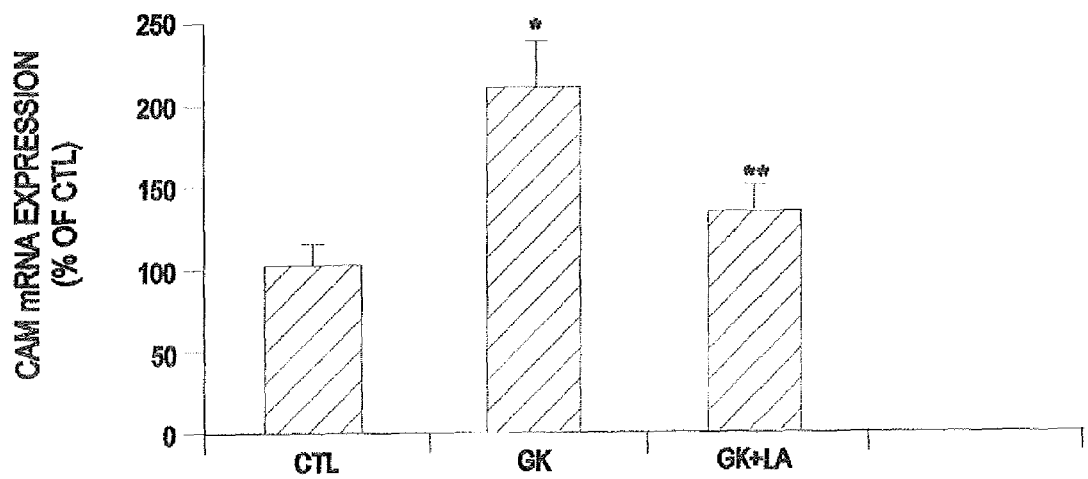
FIG. 11B is a graph illustrating ICAM-1 (CAM) mRNA expression in a control sample, a diabetic sample, and in alpha-lipoic acid-treated rats.

Further, the experiments revealed that LA counteracts diabetes-mediated up-regulation of vascular proinflammatory markers. An expression of a number of inflammatory markers, including IL-6 and ICAM-1, were measured in control, diabetic and LA-treated diabetic vessels. The results confirmed marked elevation in the vascular expression of both MCP-1 and ICAM-1 during diabetes, as shown in FIGS. 11A and 11B. This diabetic vascular proinflammatory phenotype was partially reversed with LA therapy. FIGS. 11A and 11B show vascular expression of proinflammatory mediators in control (CTL), diabetic (GK) and LA-treated diabetic rats (GK+LA). Aortic expression of IL-6 is shown in FIG. 11A and aortic expression of intracellular adhesion molecule (ICAM-1) is shown in FIG. 11B. Both were determined using QRT-PCR based techniques. Data are expressed as means±SEM of at least 7 animals/group.

The above experiments have shown that LA prevents impairment of endothelial vasodilatation induced by oxidative stress in GK rats. Specifically, during diabetes, LA attenuates the ability of oxidative stress to decrease endothelial vasodilatation by interfering with signaling through the TNF-αt/NF-κB pathway, as shown in GK rats.

Diabetes is usually accompanied by an increased production of ROS and free radicals, or by impaired antioxidant defenses, which are widely accepted as important in the development and progression of diabetes complications. Oxidative stress also facilitates endothelial cell dysfunction. In this context, attenuated endothelium-dependent acetylcholine-induced relaxation has been reported in different vascular beds of human and animal models of diabetes. A number of cellular mechanisms have been suggested to account for impaired endothelium-dependent vasodilatation, including an actual synthesis/release of hydroxyl radicals. In the above experiments, a decline in Ach-induced relaxation of rat aorta was confirmed in GK diabetic rats, which appeared to be ameliorated with LA (as shown in FIG. 1). Overall, the development of endothelial dysfunction in aortic tissue of diabetic rats is most likely linked to an exaggerated production of $O_2^-$. This enhancement in the production of $O_2^-$ may result in inactivation of NO and generation of peroxynitrite, as reflected by an increased aortic content of 3-nitrotyrosine.

The resulting decrease in NO availability might be involved in the impairment of NO dependent relaxation. Accordingly, oxidative degradation of NO caused by increased $O_2^-$ secondary to overactivity of NADH/NAD(P)H oxidase provides a reasonable explanation for the diminished response to Ach in the aorta of GK rats. It should be noted that the results do not exclude a role for other potential sources of $O_2^-$ (e.g., xanthine oxidase, mitochondrial flavoproteins) within diabetic vascular cells. Further, the observation that responses to sodium nitroprusside are altered in aortic tissue of GK rats suggests that other molecular mechanisms (e.g., diminished expression and activity of vascular smooth muscle cell guanylate cyclase) may also contribute to impaired vasodilatory responsiveness during diabetes. Both apocyanin and tiron improved Ach-induced relaxation in diabetic arteries, consistent with the concept that up-regulation of NAD(P)H oxidase activity is responsible, at least in part, for diabetes-induced endothelial dysfunction (as seen in FIG. 1). The above findings are in accordance with prior results demonstrating diminution in Ach-based vascular relaxation in human and animal model of diabetes.

The underlying cellular and molecular mechanisms associated with diabetes-related endothelial dysfunction were explored in the context of a number of possibilities, including augmented production of $O_2$—and an imbalance in the rate of reactive oxygen/nitrogen species production and disposal within the microenvironment of the vessels. With regard to this connection, lucigenin chemiluminescence measurement revealed that the aorta of GK diabetic rats exhibited a marked increase in $O_2$— production, which was inhibited by apocynin and diphenyleneiodionium (as shown in FIG. 2). It should be noted that LA action on diabetic aortic $O_2^-$ generation mimics those produced by apocynin and diphenyleneiodonium.

Additionally, the results demonstrated that diabetic vessels exhibited a marked increase in the number of ethidium bromide (EB) positive nuclei, both in the endothelium and media, when compared to non-diabetic controls (as shown in FIG. 3). Nuclear EB fluorescence was significantly reduced in LA-treated diabetic rats. This phenomenon appears to be due to an effect of LA treatment in GK vascular tissues, compared with their corresponding Wistar control values. The level of this free radical was elevated in the aortic segment of the GK rats. Thus, the LA treatment in diabetic vessels represents a compensatory mechanism to counterbalance endothelial dysfunction induced by diabetes-dependent oxidative stress.

NADH/NAD(P)H oxidase, xanthine oxidase, a dysfunctional NO synthetase, or mitochondrial flavoproteins, represent an important source for ROS generation within vascular endothelial and smooth muscle cells. These ROS based enzymatic sources are subject to alterations by a variety of physiological and pathophysiological states, including diabetes. Further, mitochondrial flavoprotein-mediated increases in $O_2^-$ generation have also been observed in bovine aortic endothelial cells cultured under hyperglycemic conditions. The NAD(P)H oxidase system constitutes a pivotal signaling element in the genesis of endothelial dysfunction and is widely accepted to account for the majority of superoxide generation in the vascular endothelial and smooth muscle cells. Thus, the hypothesis that treatment with LA attenuated the stimulation of NADH/NAD(P)H oxidase and its contributions to a diabetes related increase in vascular $O_2^-$ production was examined. This proposition is supported by the above findings, which demonstrate that an enhancement in NAD(P)H oxidase driven $O_2^-$ generation in is exhibited in diabetic aorta, and which is significantly attenuated following the LA injection (as shown in FIG. 4). The increased lucigenin chemiluminescence of diabetic vessels may be substantially inhibited by diphenyleneiodonium and apocyanin.

The vascular NAD(P)H oxidase consists of at least 3-5 subunits, with the membrane-bound cytochrome b558, $P22^{phox}$, and $gp91^{phox}$ being important for electron transport or the reduction of molecular oxygen to $O_2^-$. Apocynin acts by interfering with the NAD(P)H subunit assembly in the membrane and is therefore a more specific inhibitor than diphenyleneiodonium. Experimentation using a western blotting-based technique and qRT-PCR revealed that the protein abundance of pg91 phox and nox-1 subunits of NAD(P)H oxidase were reduced in aortic tissue of GK diabetic rats treated with LA (as shown in FIG. 5). In the above experiments, LA treatment also reduced the rate of gene expression of pg $91^{phox}$, and nox-1 subunits.

Overall, the above data are consistent with the concept that the diabetic aorta exhibits a heightened state of oxidative stress. The consequences of this phenomenon upon biological molecules, including lipids and proteins, were determined. As the above results show, with specific reference to FIGS. 6A and 6B, the levels of both protein-bound carbonyls and the thiobarbituric acid reactive substances (an indicator of lipid peroxidation) were elevated in diabetic aorta by 45% and 60%, respectively. LA treatment partially reversed the oxidative stress-mediated damage to the lipid and protein molecules during diabetes. Taken together, the inhibition of $O_2^-$ production by LA, in connection with the decreased expression of $gp91^{phox}$ and nox-1 (shown in FIG. 5) in aortic tissue of GK rats are in accordance with the concept that the NAD(P)H oxidase in the diabetic state is hyperactive and that LA, via reducing its activity and expression, may contribute, at least in part, to the overproduction of $O_2^-$ in diabetic vessels.

Figure 7B:
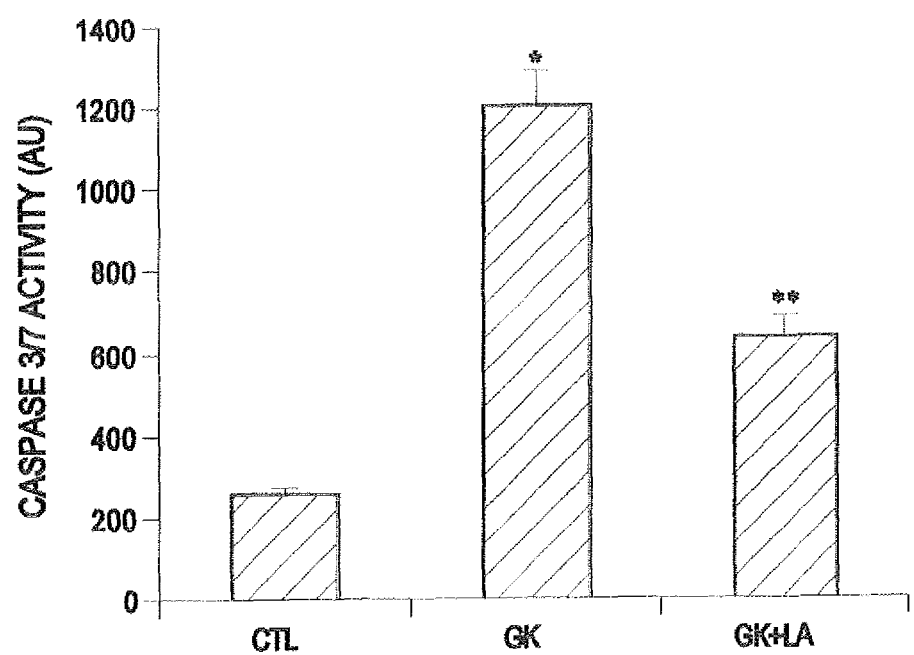
FIG. 7B is a graph illustrating caspase 3/7 activity in aortic rat vessels in a control sample, a diabetic sample, and in alpha-lipoic acid-treated rats.

Cytotoxic DNA fragmentation and caspase activities are sensitive indicators of endothelial cell death in blood vessels. Results from the above experiments revealed that the rate of DNA fragmentation in diabetic tissue was elevated by 75% over corresponding control values (as shown in FIGS. 7A and 7B). There was also an increase caspase 3/7 activity in diabetic vessels. Chronic LA treatment significantly reduced DNA fragmentation rate by 42% and caspase 3/7 by 48% in diabetic arteries. This LA-mediated antiapoptotic effect was markedly reduced two weeks after discontinuation of therapy.

Furthermore, in the above experiments, cultured arteries derived from non-diabetic control animals were exposed in vivo to TNF-α and various parameters, including $O_2^-$ generation, Ach-induced relaxation, DNA fragmentation and caspase activity, which were all measured. The data revealed that the rate of $O_2^-$ generation, caspase 3/7 activity and the levels of DNA fragmentation were elevated in response to TNF-αc treatment (as shown in FIGS. 9A, 9B and 9C). In contrast, this proinflammatory cytokine impaired Ach-induced vasorelaxation. Additionally, pre-treatment with LA partially reversed the above TNFα-induced abnormalities. It is well established that TNFα enhances the activity of NF-κB probably via $H_2O_2^-$ mediated mechanisms. The experimental data revealed that the NF-κB level is high in vascular diabetic nuclei, and that this abnormality was reversed with LA chronic therapy, as shown in FIGS. 10A and 10B.

Factors affecting the expression of endothelial adhesion molecules, therefore, are important in regulating vascular inflammatory processes. Activation of the transcription factor NF-κB; e.g., by inflammatory cytokines, is required for the transcriptional activation of endothelial cell adhesion molecules. Unlike most other cell types, NF-κB activation in endothelial cells can also lead to cell death. In the above experiments, it was found that LA inhibits NF-κB activation and adhesion molecule expression in aortic tissue of GK rats. The data demonstrate that LA effectively inhibits TNF-α-stimulated mRNA and TNF-α-plasma concentration (shown in FIGS. 8A and 8B) and consequent attenuated endothelial vasodilatation (shown in FIGS. 9A, 9B and 9C), as well as LA inhibiting NF-κB protein expression (shown in FIGS. 10A and 10B). These findings correlate well with the finding that LA also improves cell survival.

In the above experiments, an expression of a number of inflammatory markers, including IL-6 and intracellular adhesion molecule (ICAM-1), were measured in control, diabetic and LA-treated diabetic vessels. The results confirmed marked elevation in the vascular expression of both MCP-1 and ICAM-1 during diabetes (as shown in FIGS. 11A and 11B). This diabetic vascular proinflammatory phenotype was partially reversed with LA therapy. The data that LA inhibits mRNA expression for ICAM-1 and IL-6 indicates that LA inhibits binding of NF-κB to the upstream regulatory promoter sequences of these genes. The data strongly suggest that LA inhibits TNF-α-induced endothelial activation by affecting the NF-κB/IKK signaling pathway at the level (or upstream) of IKK, rather than by preventing DNA binding of NF-κB.

This conclusion is further supported by observations that LA also inhibits diabetes-induced adhesion molecule expression in aortas of GK rats and NF-κB activation in other cells. NF-κB has been proposed to be a redox-sensitive transcription factor. In most cell types, NF-κB can be activated by a diverse range of stimuli, suggesting that several signaling pathways are involved.

The observed anti-inflammatory action of LA in aortic tissue of GK rats extends to many other important mediators of inflammation, in a variety of cells and tissues. It is believed that LA exerts vasculoprotective effects via mechanisms involving the downregulation of the TNFα/NF-κB signaling pathway.

The hypothesis that lipoic acid modulates the TNF-α/NF-κB pathway was also tested in fibroblasts from diabetic Goto Kakasaki rats and matched Wistar control rats. A wealth of evidence indicates that chronic oxidative stress can alter the sensitivity and the mechanism by which a cell dies in response to various stressors. Accordingly, the effect of hydrogen peroxide (HP; the most common endogenous oxidant) on cell viability and lactate dehydrogenase (LDH) release into the cultured medium in control fibroblasts (CFs) and diabetic fibroblasts (DFs) was evaluated.

Figure 12A:
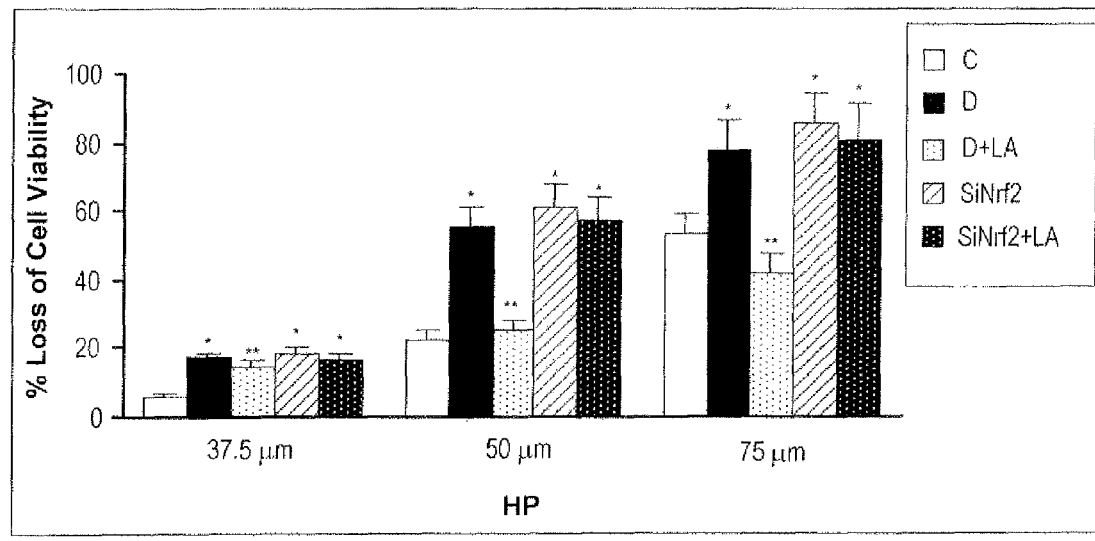
FIG. 12A is a chart showing the effect of various concentrations of hydrogen peroxide (HP) on cell viability among control fibroblasts and diabetic fibroblasts, and that alpha-lipoic acid protected both cell types from hydrogen peroxide in a Nrf2-dependent manner.
Figure 12B:
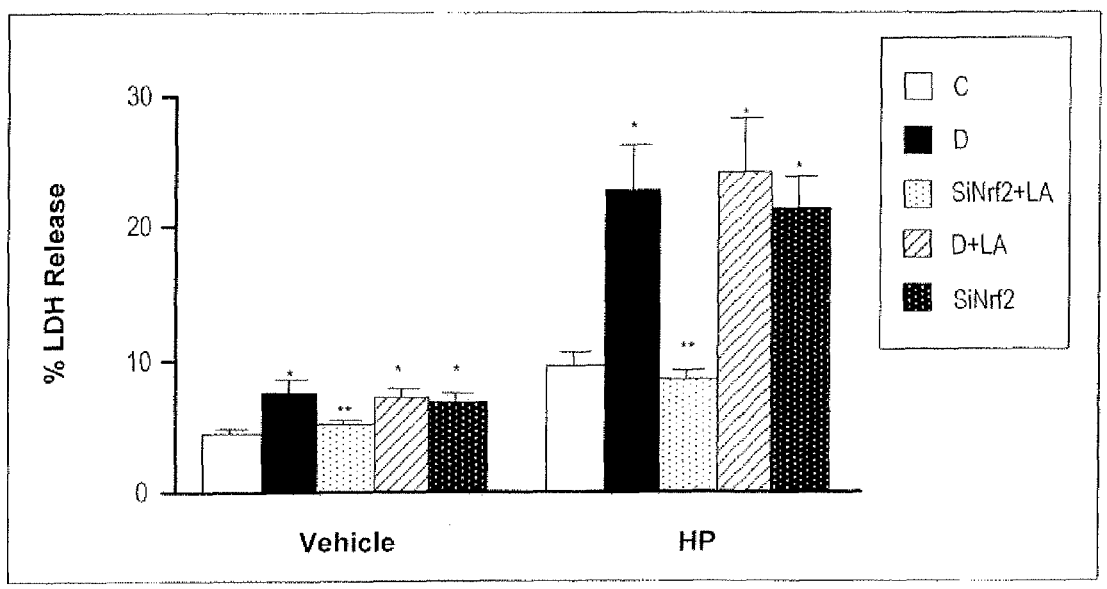
FIG. 12B is a chart showing that in response to hydrogen peroxide (HP), the rate of lactate dehydrogenase (LDH) release into cell culture media, which is a measure of necrotic cell death, is markedy enhanced in DFs when compared to corresponding control values, and that alpha-lipoic acid reduces cell death in a Nrf2-dependent manner.

The resulting data showed that exposure of DFs to 37.5, 50, and 75 uM HP for 16 hours led to a 17%, 55% and 78% loss in cell viability, respectively, as shown in FIG. 12A. However, exposure of normal cells to the same concentrations of HP resulted in less marked changes in cellular viability of only 6%, 22%, and 53%, respectively. A necrotic mechanism, rather than an apoptotic mechanism, appears to mediate the increase in hydrogen peroxide-induced cell death during diabetes. Indeed, our data depicted in FIG. 12B showing that, in response to HP, the rate of LDH release into cell culture media (a measure of necrotic cell death) was markedy enhanced in DFs when compared to corresponding control values gives credence to this suggestion.

Figure 12C:
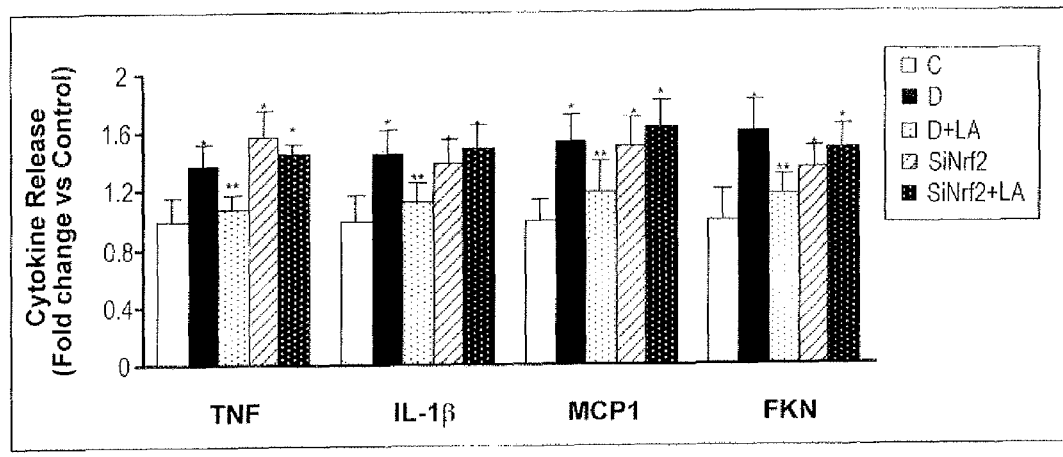
FIG. 12C is a chart showing that diabetic fibroblasts release higher amounts of inflammatory cytokines, and that this phenomenon is ameliorated by alpha-lipoic acid in a Nrf2-dependent manner.
Figure 12D:
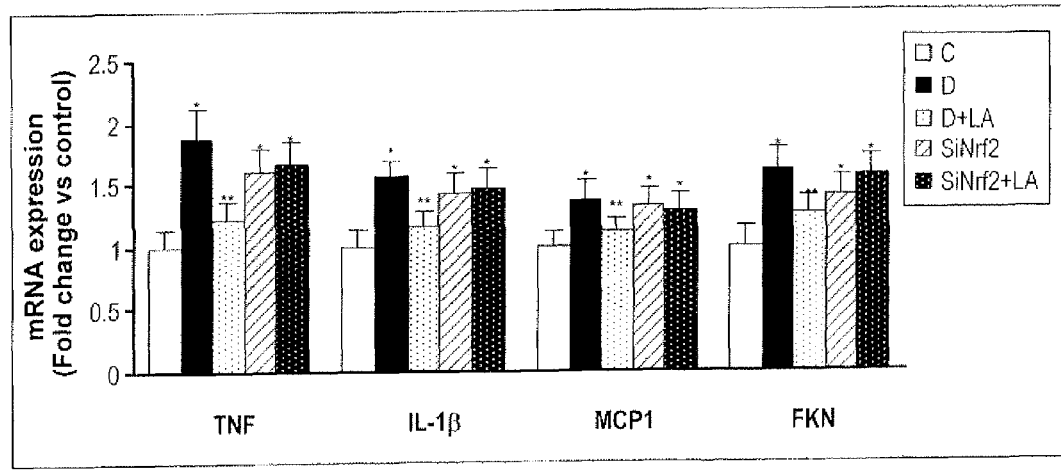
FIG. 12D is a chart showing that transcription of inflammatory cytokines is increased in diabetic fibroblasts, and alpha-lipoic acid decreases inflammatory cytokine transcription in an Nrf2-dependent manner.

Further experiments confirmed that the above enhancement in necrotic cell death during diabetes was accompanied by a marked increase in the expression and rate of release of pro-inflammatory cytokines, including TNF-α, IL-1β fractalkine and MCP1, as shown in FIGS. 12C and 12D. Interestingly, most of the above abnormalities, including the state of low-grade inflammation and the increase in necrotic cell death, were ameliorated following treatment with lipoic acid.

The aforementioned anti-necrotic and anti-inflammatory effects may be mediated by an Nrf2-dependent signaling pathway. Consistent with this proposition is the data documenting that knocking down Nrf2 using siRNA silencing technique negated the beneficial effects of lipoic acid.

The beneficial effects of lipoic acid for diabetic tissues led to testing of α-LA in other contexts. It was found that lipoic acid protects against apoptotic/necrotic death after chemotherapeutic treatment of HEK293 cells by inducing the expression of NF-κB. Therapeutic toxicity remains the most challenging aspect of treating patients with cancer. Protecting normal cells from therapy-induced cellular death may be of great benefit to patients and workers (firemen, nuclear plants, etc.) who are exposed to abnormal levels of therapeutic or environmentally related chemicals or radiation. Alpha-lipoic acid emerged as a molecule capable of significantly protecting cells from endogenous and exogenous molecules associated with cellular death by necrosis and apoptosis.

Figure 13A:
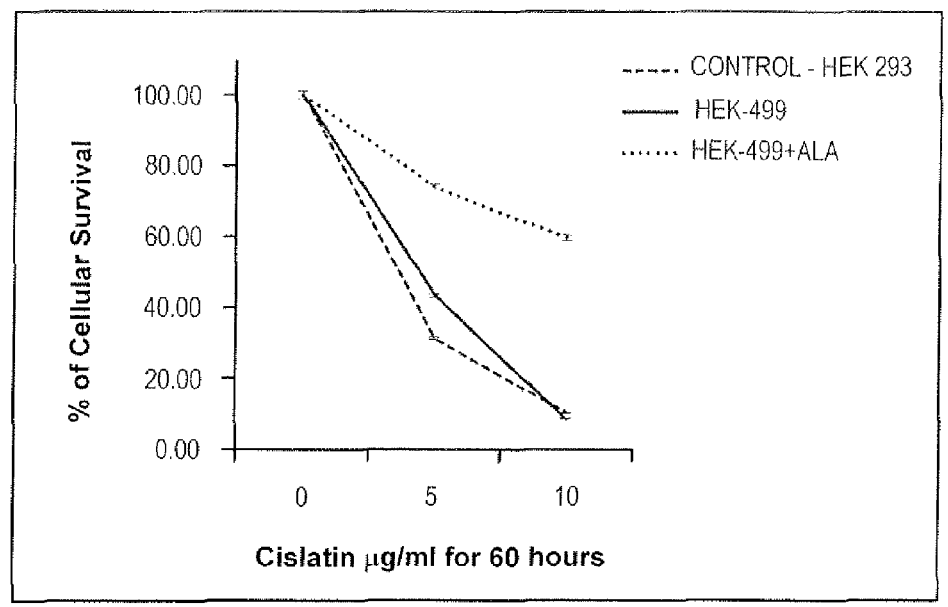
FIG. 13A is a graph showing that alpha-lipoic acid increases the viability HEK-499 cells, a cell line already engineered to be resistant to chemical and radiological damage, when exposed to otherwise lethal doses of the cancer chemotherapeutic cisplatin.
Figure 13B:
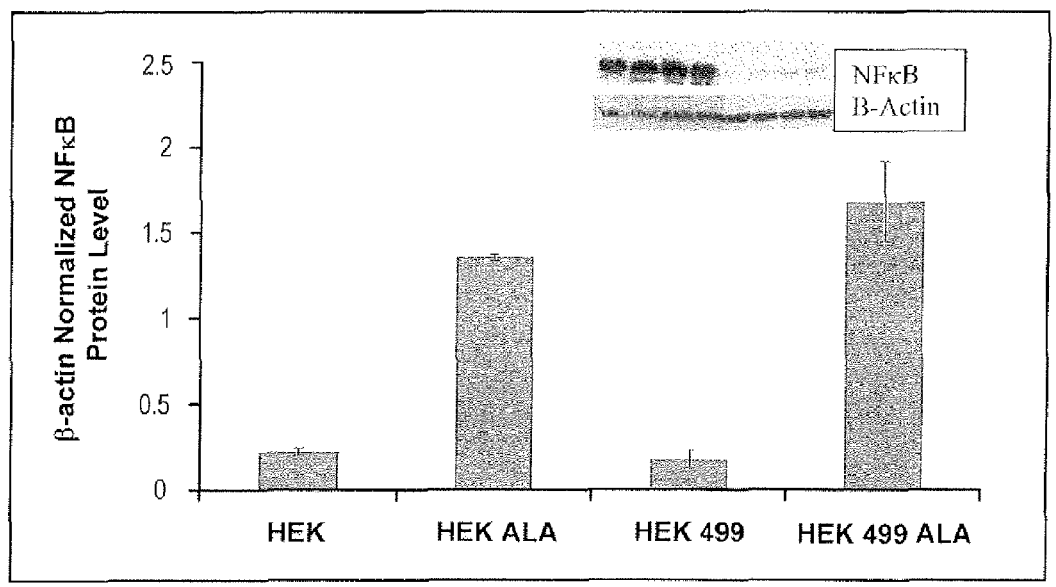
FIG. 13B is a graph showing that a significant increase in the expression of NF-κB in HEK-499 and HEK-293 (parental cells) correlates with exposure to alpha-lipoic acid and cell survival in cells incubated with lethal doses of cisplatin.

Alpha-lipoic acid increased HEK-499 cells, which were engineered to be resistant to chemotherapies and radiotherapies by depleting Raf Kinase inhibitory protein resistance to lethal doses of cisplatin, a chemical used in cancer therapy. The cells were significantly protected by addition of 500 microMolar α-lipoic acid in the cellular media prior to treatment with cisplatin at variable doses, as shown in FIG. 13A. We show that cellular protection is achieved by the induction of NF-κB in HEK-499 cells, a molecule known for its anti-apoptotic activity in various cells (excluding endothelial cells). FIG. 13B shows the significant increase of NF-κB in HEK-499 and HEK-293 (parental cells) using western blotting. The inset shows four cell samples exposed to α-lipoic acid on the left, and four control cell lines (not exposed to α-lipoic acid) on the right.

These data illuminate for the first time that α-lipoic acid protects cells against $H_2O_2$ and cisplatin by up-regulating NF-E2-related nuclear factor 2 (NRF2) responsive genes and NF-κB, respectively. The data demonstrate that the response of a cell to α-lipoic acid is determined by its individual physiology and genetics. It also demonstrates for the first time that response to NF-κB and TNF-α is tissue specific, and cannot be predicted generally. This claim has immense benefit to patients with diabetes, where cellular death by necrosis/apoptosis is a major mechanism in diabetes-related complications. Moreover, the cellular protection by α-lipoic acid against apoptotic and necrotic death may be of significant value in myocardial infarction, and in protection of normal cells against exogenous chemotherapeutics, conditions frequently encountered by cancer patients and workers that may be exposed to hazardous chemicals or radiation.

It is to be understood that the present invention is not limited to the embodiment described above, but encompasses any and all embodiments within the scope of the following claims.

We claim:

1. A method for determining efficacy of an alpha-lipoic acid treatment for treating a subject suspected of suffering from diabetes-related vascular complications, the method comprising the steps of:

determining a level of at least one biomarker selected from the group consisting of inflammatory biomarkers and apoptotic biomarkers in at least one sample obtained from the subject following administration of the alpha-lipoic acid, wherein an initial dosage rate thereof is between approximately 100 mg and approximately 300 mg per day, wherein the at least one biomarker is selected from the group consisting of TNF-α, IL-1β, IL-6, MCAP-1, NF-κB, caspase 3, caspase 7, pg-91$^{phox}$, Nox-1, ICAM-1, PI3K, and Akt; and comparing the level of the at least one biomarker in the at least one sample obtained from the subject with a known standard level of the inflammatory or apoptotic biomarker associated with diabetes-related vascular complications;

wherein a lower level of the at least one biomarker in the at least one sample from the subject relative to the known standard level of the at least one biomarker indicates that the alpha-lipoic acid treatment is efficacious for the treatment of diabetes-related vascular complications in the subject.

2. The method for determining efficacy of claim 1, wherein said at least one biomarker comprises TNF-α and caspase 3 in combination.

3. A method of treating diabetes-related vascular complications, comprising the steps of:

obtaining a pre-treatment sample from a patient exhibiting signs or symptoms of diabetes-related vascular complications;

testing the pre-treatment sample to determine levels of at least one biomarker selected from the group consisting of inflammatory biomarkers and apoptotic biomarkers to determine pre-treatment levels of the at least one biomarker, wherein the at least one biomarker is selected from the group consisting of TNF-α, IL-1β, IL-6, MCAP-1, NF-κB, caspase 3, caspase 7, pg-91$^{phox}$, Nox-1, PI3K, and Akt;

administering to the patient an initial dosage rate of alpha-lipoic acid or pharmaceutically acceptable salts thereof for the treatment of the diabetes-related vascular complications, wherein the initial dosage rate thereof is between approximately 100 mg and approximately 300 mg per day;

obtaining a post-treatment sample from the patient;

testing the post-treatment sample to determine levels of at least one biomarker selected from the group consisting of inflammatory biomarkers and apoptotic biomarkers to determine post-treatment levels of the at least one biomarker; and increasing the dosage rate of the alpha-lipoic acid when the post-treatment levels fail to show significant reduction from the pre-treatment levels of the at least one biomarker.

* * * * *